US006820235B1

(12) United States Patent
Bleicher et al.

(10) Patent No.: US 6,820,235 B1
(45) Date of Patent: Nov. 16, 2004

(54) CLINICAL TRIAL DATA MANAGEMENT SYSTEM AND METHOD

(75) Inventors: Paul A. Bleicher, Newton, MA (US); Nicholas Stamos, Belmont, MA (US); Jeffrey P. Klofft, Marlborough, MA (US); Richard M. Dale, Newton, MA (US)

(73) Assignee: Phase Forward Inc., Newton, MA (US)

( * ) Notice: Subject to any disclaimer, the term of this patent is extended or adjusted under 35 U.S.C. 154(b) by 0 days.

(21) Appl. No.: 09/092,441

(22) Filed: Jun. 5, 1998

(51) Int. Cl.[7] ................. G06F 15/00; G06F 17/24; G06F 17/60

(52) U.S. Cl. ............. 715/501.1; 715/512; 715/513; 705/2; 600/300

(58) Field of Search ............. 707/501.1, 104.1, 707/104; 705/2, 3; 600/300; 348/161; 435/6; 715/501.1, 512

(56) References Cited

U.S. PATENT DOCUMENTS

| 5,325,478 | A | | 6/1994 | Shelton et al. |
| 5,606,609 | A | | 2/1997 | Houser et al. |
| 5,660,176 | A | * | 8/1997 | Iliff ............................. 600/300 |
| 5,666,490 | A | | 9/1997 | Gillings et al. ............. 709/238 |
| 5,737,739 | A | * | 4/1998 | Shirley et al. .............. 715/512 |
| 5,772,585 | A | * | 6/1998 | Lavin et al. ................ 600/300 |
| 5,813,009 | A | | 9/1998 | Johnson et al. |
| 5,826,237 | A | * | 10/1998 | Macrae et al. ................. 705/2 |
| 5,893,109 | A | * | 4/1999 | DeRose et al. .......... 707/104.1 |
| 5,973,731 | A | * | 10/1999 | Schwab ...................... 348/161 |
| 5,991,731 | A | * | 11/1999 | Colon et al. .................... 705/3 |
| 5,997,476 | A | * | 12/1999 | Brown ........................ 600/300 |
| 6,022,315 | A | * | 2/2000 | Iliff ............................. 600/300 |

(List continued on next page.)

FOREIGN PATENT DOCUMENTS

| WO | WO97/44752 | 11/1997 |
| WO | WO98/12669 | 3/1998 |
| WO | WO98/39720 | 9/1998 |
| ZA | 981670 | 2/1998 |

OTHER PUBLICATIONS

Harlan, William R., Creating an NIH clinical trials registry: A user–friendly approach to health care, JAMA, Chiacago, Jun. 8, 1994, vol. 271, issue 22, start p. 1729.*

(List continued on next page.)

*Primary Examiner*—Joseph Feild
*Assistant Examiner*—William L Bashore
(74) *Attorney, Agent, or Firm*—Hamilton, Brook, Smith & Reynolds, P.C.

(57) ABSTRACT

A system and method for managing clinical trial data includes dynamically generating, at a server, a data entry form to be displayed at a client. The data entry form is generated dynamically in a SGML-derived language. Control elements within the form comprise images which are used to construct the control elements and larger controls. The form is generated from a protocol database and a context received from the client, is populated from the data database, and is published to the client. Templates based on the protocol database comprise several frames including intermediate frames for displaying frame borders which are non-horizontal and non-vertical. If the trial protocol changes during a trial, the generated form is based on the protocol version active at the time data was entered into the form. Inadvertent use of the application is discouraged requiring an authentication procedure and displaying a picture of the authenticated user. Furthermore, help is provided by creating a link between the text or each question and information about the question. The source of help may be any or all of a protocol document, an investigative brochure, and a study guide. In addition, a user, upon logging in, is presented with a dashboard screen which provides information or links to information such as trial-related news, alerts, statistical information, progress reports and a list of work to be completed.

49 Claims, 17 Drawing Sheets

U.S. PATENT DOCUMENTS

| | | | |
|---|---|---|---|
| 6,029,138 A * | 2/2000 | Khorasani et al. | 705/2 |
| 6,108,635 A * | 8/2000 | Herren et al. | 705/2 |
| 6,149,585 A * | 11/2000 | Gray | 600/300 |
| 6,218,122 B1 * | 4/2001 | Friend et al. | 435/6 |
| 6,272,506 B1 | 8/2001 | Bell | |
| 6,415,295 B1 * | 7/2002 | Feinberg | 707/104.1 |
| 6,496,827 B2 | 12/2002 | Kozam et al. | |

OTHER PUBLICATIONS

Van Camp, Ann J., Databases for nurses: Special subjects, Database, Weston, Feb. 1994, vol. 17, issue 1, start p. 103.*

Oliver, Dick et al., Netscape Unleashed, 1996 Sams.net Publishing, pp. 118–121, 376–379.*

Sauer, F. et al., Multimedia technology in the radiology department, ACM International Multimedia Conference, Oct. 15–20, 1994, pp. 263–269.*

Kiuchi, T. et al., "Automated generation of a World Wide Web–based data entry and check program for medical applications," *Computer Methods and Programs in Biomedicine* 52:2 pps. 129–138 (Feb. 1997).

Kelly, M.A. et al., "The Internet and randomised controlled trials," *International Journal of Medical Informatics* 47:1–2 pps. 91–99 (1997).

"Multi–State Button Manipulation using a Single Graphic," *IBM Technical Disclosure Bulletin* 38:4 pps. 585–587 (Apr. 1995).

"Efficient 3D Buttons in Dynamic Hyper Text Markup Language Pages," *IBM Technical Disclosure Bulletin* 41:1 pps. 695–698 (Jan. 1998).

Girgensohn A. et al., "Seamless integration of interactive forms into the Web," *Computer Networks and ISDN Systems* 29:8–13 pps. 1531–1542 (1997).

Netscape Communications Copr.: "NetHelp" Nethelp Release 1.0 SDK Documentation, Online! –Aug. 1996 pps. 1–14 <URl:http://home.netscape.com/eng/help/sdkl/sdk-site.html>.

* cited by examiner

Application Layout

Jennifer Smith, RN
Clinical Research Coordinator

Home | Help | Logout
Enrollment
Visits
Queries
Status
Documents

JPH/OI: Wk-4 Dem
JPH/OI: Wk-4 ECG
JPH/OI: T¢E Schec
Site OI GRBs

Form Layout 253

Week-4 Week-2 Week1 Week2 Week3 Week4 Week5 Week6 Week7 Week8

| IF | DEM | HH | SS | PE | VS/BP | ECG/CXR | LAB | CM |

■ Ready for SDV   Patient: JPK   Patient No: OI-OOI

Demographics

Demographics — 557A  557B  557C  556

1. Gender: ○ Male  ● Female
2. Date of Birth: Feb ▼  19 ▼  1964 ▼
3. Race/Ethnic Origin: ● Black ▼   ○ Other (specify) [    ]
4. Height: [66] ● In  ○ cm
5. Weight: [145] ● lb  ○ kg
6. Frame: Medium ▼
   Calculated weight variance from avg. ___ % Above/Below Application Data Smoking History 7. Has patient ever smoked?   ○ Yes  ● No  ○ Not Done
   *You indicated that the patient smokes cigarettes in item 9. Please check that no is the correct answer to "Has the patient ever smoked?"*
8. If the patient has ever smoked, has the patient quit smoking?   ○ Yes  ● No  ○ Not Done
9. If the patient currently smokes, the patient smokes:   ☑ Cigarettes  ☐ Cigars
   ☐ Pipe  ☐ Not Done
10. If the patient has ever smoked cigarettes, enter the average number of packs smoked per day:  ● [1]  ○ Unknown  ○ Not Done

[Submit] [Cancel]

CLINICAL TRIAL DATA MANAGEMENT SYSTEM AND METHOD

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Once a pharmaceutical, medical device manufacture or bio-technology company has developed a treatment, device or drug therapy, approval from a regulatory authority, such as the FDA in the US, must be obtained before it can be made available through prescription. The submission to the regulatory authority consists of a large volume of information, including clinical information which focuses on the safety and efficacy of the therapy. Much of that information is collected by conducting clinical trials.

A pharmaceutical, medical device manufacture or bio-technology company sponsors a series of clinical trials. Either an internal clinical group manages these trials or they are out-sourced to a clinical research organization (CRO). The clinical group or CRO contracts with investigation sites that in turn recruit patients for the study and collect the clinical data.

The clinical trials are performed in a series of phases, known as Phase I, Phase II, Phase III, and Phase IV. Each phase varies in duration, the number of patients involved and purpose. Failure at any stage of Phases I, II or III of the clinical trial process effectively ends the therapy's chances for final approval.

Before entering Phase I, the sponsor needs to obtain regulatory approval. Phase I trials typically last six months and involve tens of volunteer subjects usually all of whom are located at a single investigative site. Phase I trials test the safety of the therapy. Once Phase I rials are complete and the therapy has been shown to be safe, the sponsor requests permission from the regulatory authority to proceed with further clinical tests.

Phase II trials typically last six to twelve months, involve tens to hundreds of patients and are conducted to test the effectiveness of the treatment, device or drug. A sponsor may conduct many Phase II trials, attempting to find as many uses of the therapy as possible. If the therapy appears to be effective, the sponsor requests permission from the regulatory authority to proceed with large scale trials.

For each likely use of the therapy, the sponsor conducts at least two Phase III trials. Phase III trials typically last 24 to 36 months and involve thousands of patients. Phase III trials are blinded trials, that is, a portion of the patients receive the therapy and the remaining patients receive a placebo or active control, and the identities of patients taking the trial therapy are not known to anyone until the trial is complete. Phase III trails are conducted to test the safety and effectiveness of a therapy in a large population. The Phase III trial is the first opportunity to observe infrequent adverse effects in the general population; each and every one is carefully recorded. Since the effectiveness of the therapy is tested in a blinded environment, the results are not known until after the study is complete.

Phase IV trials occur after approval and are generally held to obtain approval to change a characteristic such as the delivery system, e.g., from liquid to tablets, or to change the status, e.g., from a prescription drug to an over-the-counter drug. Failure at any stage of a Phase IV trial effectively ends the therapy's chances of obtaining approval for such a change.

Every clinical trial has a protocol which specifies the exact timing and nature of the measurements and interventions to be performed on each patient. The protocol's time-line lists a series of events, or visits, where the data are collected from the study patient. The time-line of a typical study starts with the screening and enrollment of a patient and typically ends with the last patient visit.

FIG. 1 illustrates the preparation and processing of paperwork in a typical clinical trial. There are a number of points in the process where the data are audited and reviewed. A patient 401 visits the investigative site 413. For each visit, the protocol instructs the investigator to collect certain information 403 about the patient 401. After the information 403 is collected, it is recorded on a Case Record Form (CRF) 405. Periodically, a Clinical Research Associate (CRA) 417 visits the investigative site 413 and compares the data in the original medical record 403 with the information on the CRF 405. This process 406 is known as source document validation, or SDV.

Once the CRF has been source document verified, CRF 405 is delivered to the organization 407 running the trial (either a CRO or an internal clinical group at he sponsor) as indicated by arrow 408. When the CRF 405 arrives at the sponsor/CRO 407, its data is entered into a clinical database 409 twice to ensure that no errors are introduced, as indicated by arrows 410A and 410B.

A medical monitor 415 and clinical data manager (CDM) 419 at the sponsor/CRO 407 examine the CRF 405 to look for inconsistencies. If any of the data are incomplete or appear incorrect, the CRF is sent back to the investigative site 413 with a query 411 for correction, a process known as cleaning. If someone at the investigative site 413 makes a change as a result of a query 411, the data is again source document verified by the CRA 417, and is sent back to the sponsor/CRO 407 for data entry, as identified by arrow 412. When all of the data cleaning is complete, the clinical database 409 is locked and data analysis begins.

As can be seen, a large volume of data is collected during each clinical trial, and the collection and management of clinical data is a large problem that requires many people performing a number of different and unique roles. These roles fall into three groups: the investigative site roles, the clinical data review roles, and other central sponsor roles.

SUMMARY OF THE INVENTION

Implementing such a system or method on the Web has the obvious advantage of ease—many people are now familiar with Web technology and even those with computerphobia are becoming comfortable accessing the Web. In addition, because browsers are so inexpensive, while the personal computers on which they run can typically be had for under $1,000, there are no major expenses involved for other than the development of the clinical trial database. No special software needs to be distributed.

On the other hand, one disadvantage is that access over the Web can be considerably slower than a direct connection to a host server. Another is that certain things that can be done easily in a closed environment with custom software, such as curved boundaries between frames, are not so readily done on the Web. The present invention is aimed at overcoming these and other disadvantages.

Therefore, a method of implementing a graphical user interface (GUI) control element within a client browser, comprising creating several bitmaps which can be constructed to present the GUI control element in a variety of different states. A Standard Generalized Markup Language (SGML)-derived language such as HTML or XML is used to specify placement of the bitmaps within a document. Upon receipt of the document, a browser displays a desired GUI control.

Preferably, placement of he bitmaps is specified by placing indicators such as URLs corresponding to the bit maps in certain locations, preferably table entries, within the document, such that the browser will correctly display the control element. Preferably, these bit maps are used by many similar GUI Controls.

Furthermore, a bitmap may be partitioned into multiple sections, where each section is associated with a different indicator.

In particular, in a preferred embodiment, one type of control element is a button control which comprises left, right, top and bottom pieces. A label is placed between the top and bottom pieces.

Another type of control element is a file tab, or tab, control, comprising left, right, top and bottom pieces. A label is placed between the top and bottom pieces. Multiple tab controls can be grouped together, sharing bitmaps which have a left or right overlapping piece. Different bitmaps also provide different styles such as color to portray a selected or non-selected tab.

Yet another type of control is a linear control which comprises button control elements spaced at intervals along a line. Each button control element has a corresponding bit map or combination of bit maps. A pointer indicating a current value along the line also has an associated bitmap.

In the preferred embodiment, the server is stateless with respect to the GUI controls. That is, when a request is received, the server has no knowledge of he states of the controls other than what is sent in the request.

The present invention also provides a method of entering clinical trial data from a client, where the data is maintained on a server. A data entry form to be displayed at the client, is generated at the server dynamically in a SGML-derived language, from a library of code fragments. The form is generated according to the user, the patient, the protocol version within a clinical trial and data previously entered.

In a preferred embodiment, a protocol, or clinical, database is created which is specific to an application. A data database is created which is specific to a subject processed by the application. Then the form is generated based on the protocol database, preferably based on a clinical protocol, and a context received from the client. Preferably this is done by generating a template based on the protocol database and a context received from the client. The form or template is populated with application data from he data database, and published to the requesting client browser.

Preferably, the template comprises several frames including control frames with one or more control elements. An intermediate frame presents a visual attribute shared by the control frames. The appearance of the intermediate frame depends on the visual appearance of the control frames.

In addition, in a preferred embodiment, protocols can be changed during the trial. The generation of the template is then further based on the protocol version which was active at time of entering data to be displayed. Thus the form to be displayed is itself based on the protocol version which was active at time data was entered.

Furthermore, in a preferred embodiment, rules are associated with the displayed form, and are based on he protocol version which was active at the time of entering data to be displayed in the form.

Yet another aspect of a preferred embodiment of the present invention is the discouragement of inadvertent use of a computer application, by requiring a log-on procedure for each user, and displaying a picture of the currently logged-on user.

Still another aspect of a preferred embodiment of the present invention is the provision of context-sensitive help. Preferably, a displayed form has at least one question to which a user must respond to provide clinical data. Links are created between the text of each question and detailed information related to the question. If the user clicks on text of the question, detailed information corresponding to the question is retrieved from the server is displayed.

Preferably, the detailed information is derived from any or all of three source documents defining the clinical trial: a protocol document, an investigative brochure, and a study guide. Preferably, the user can walk through each of he documents.

Another aspect of the present invention is the dashboard screen which provides information regarding the trial, customized for the user and presented to the user upon logging in to the system. Such information preferably includes but is not limited to trial-related news, alerts, statistical information, progress reports and a list of work to be completed

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4A is a diagram illustrating a Web page comprising a typical clinical form created by the present invention.

FIGS. 4B and 4C are illustrations depicting the hierarchical structure of a form such as that of FIG. 4A within the present invention.

FIGS. 13A–13F are diagrams illustrating the use of context sensitive help as employed by the present invention.

DETAILED DESCRIPTION OF THE INVENTION

The present invention provides a means of expediting the process by collecting and managing trial data including communications between sites over the Internet, using a World Wide Web (Web) server in combination with Web browsers which run on most personal computers. Such a system requires little to no investment. Communication between parties is near-instantaneous, and can be saved as part of the record. Checks can be performed automatically and instantaneously. This allows faster process no of the data, and faster availability of the data. A significant amount of time is cut out the trial time, allowing the sponsor to get its product to market sooner, saving millions of dollars, and potentially aiding thousands or millions of potential recipients of the treatment much sooner than the treatment might otherwise be available.

The Internet is a world-wide computer network which actually comprises thousands of smaller networks connected to the Internet backbone, thus linking millions of computer users around the world. The Web is a technology which allows a user to format a document according to some standard. The document is made accessible to a Web server which transmits the document to another user upon request. When the document is received by the requestor running a Web browser, the browser knows how to construct and display, or render, the document.

Requests are made to a Web server using a Uniform Resource Locator (URL) which identifies the Web server and the specific document. These documents are often called Web "pages".

One common format for transmitting these documents is known as Hypertext Markup Language (HTML). HTML allows the creator of a document to specify the appearance and placement of a variety of things such as font size, style, headers and so, including placement of data or pictures within tables.

If a Web page is to contain pictures, these pictures or images are often specified within the document by their respective source locations, where they are stored as image files using formats such as "gif" or "jpeg", for example. These image files can be quite large and can consume an annoyingly large amount of time as a requesting party waits for the image files to download. Of course, this is compounded when there are several image files to be downloaded.

One feature of most Web browsers is the ability to cache information locally. Thus image files can be stored in the browser's cache, so that if the user requests the same pace at a later time, the browser uses the locally cached image files rather than downloading the files again. While this saves much of the time that would otherwise be wasted re-downloading the images, it does come with a cost: image files can be large and caching many of theme for hundreds or thousands of Web pages can consume a significant portion of local memory or disk space.

Figure 1:
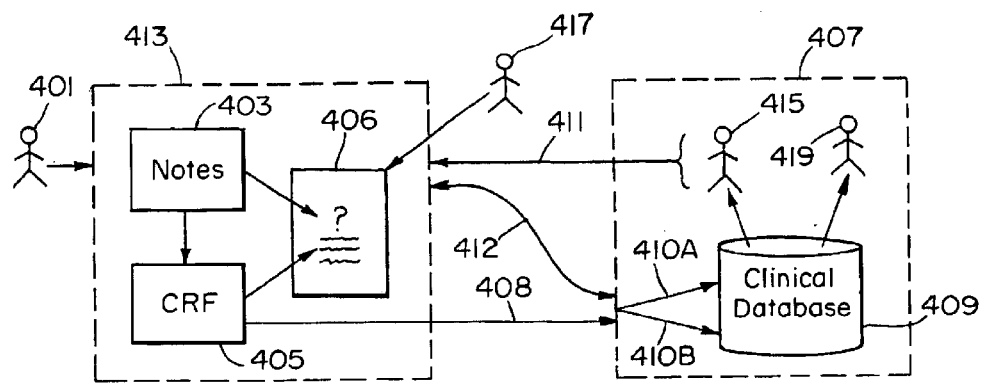
FIG. 1 is a block diagram illustrating current trial data collection practice.
Figure 2:
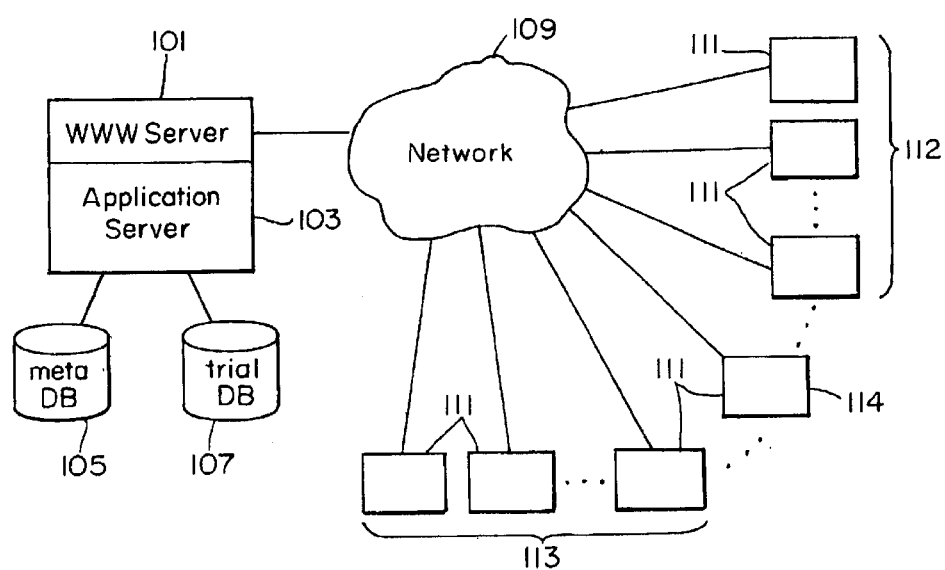
FIG. 2 is a block diagram illustrating the present invention's implementation of a clinical trial data management system operating over the Internet and the World Wide Web.

FIG. 2 illustrates the present invention operating over the Internet. The Clinical Research Organization (CRO) or the sponsor's own internal clinical group responsible for maintaining trial data maintains an application server 103 which stores data about the protocol, the forms to be used, the roles of various individuals involved, etc., in a mete database 105. Actual clinical data collected during a trial is maintained in a trial database 107. Of course, while there are logically two databases, the actual data can be maintained in just one or many databases.

The application server 103 receives requests via a network 109, such as the Internet, from users 111 at the investigative sites 112, sponsor sites 113, and CRO sites 114, and responds to the requests, presenting a consistent and secure interface through a Web server 101. The Web server 101 transmits information to the requesting site as a document formatted according to an SGML-derived language, such as XML, or preferably, hypertext markup language (HTML) document. The document can also include small scripts in a language such as Javascript for implementing certain rules at the user's site. Investigative sites 112 include, but are not limited to, hospitals, clinics and independent doctors' offices.

During a clinical trial, various individuals have certain responsibilities which are accompanied by privileged access to certain documents. In the present invention, these privileges are rigidly defined. Roles are defined as a collection of privileges such that assigning a particular individual to a defined role bestows upon that individual the collection of corresponding privileges.

For example, in the present invention, there are two primary roles at the investigator site. The Clinical Investigator and the Clinical Research Coordinator (CRC) gather the data for the trial according the protocol, and record the data on CRFs which are sent to the sponsor for review and acceptance.

The Clinical Investigator (CI) is responsible for treating his patients and executing the study protocol. He has the ultimate responsibility for all activities at his site.

The CRC is responsible for collecting all of the information about the patients in the study who are being treated at the CRC's site, and for returning the information to the clinical group. In the US this individual is typically a nurse, while in Europe the role of the CRC is typically performed directly by the Clinical Investigator.

The people fulfilling these roles at the investigation site must be able to see information about all of their patients who have been screened or accepted into the study. This information includes a patient's visit history, the contents of the CRF associated with the patient, and the patient's lab results to name a few.

As clinical reviewers at the CRO or sponsor examine the answers to the CRF questions, they may have questions or comments which require responses from the investigation site. These questions and comments are referred to as queries. The CI or CRC must be able to respond to a query, usually by attaching a comment to a question or CRF, by adding new or additional information to a CRF, or by changing information previously entered on the CRF. This is a key component of data cleaning. Once the query is resolved, the response is returned to the individual reviewer who issued the query.

During the course of a trial, some patients may experience adverse events. These events are noted by recording a text description of the even, as well as a medical code for that even. These codes are found in a number of coding dictionaries such as COSTART. If the adverse event is serious, the sponsor is notified immediately.

Some patients in the trials may take other medications during the trial. These medications, whether taken regularly as for allergy medication, or occasionally such as aspirin for a headache, are 'coded' and stored in the patient's record.

From time to time, the CI or CRC at the investigation site must review some of the information about the study such as the study protocol, the study reference manual, a study newsletter, and a list of frequently asked questions. In addition, they must review information about individual questions on the CRF such as getting a list of all previous responses to a question and viewing the discrepancy criteria for a question.

During a trial, a CI or CRC may need to communicate with a representative of the sponsor. For example, initially the CI/CRC needs to provide information about the site to the sponsor (Form 1571, lab normals, CVs of the investigator). As the study progresses, the CRC may have a question or may notice something that would interest the sponsor. Much of this communication is included in the study files.

In addition to communication with the sponsor, the investigation site may want to communicate with another site. Perhaps an investigation site wants to ask someone at another site a question. These communications are not part of the study data.

In addition to written communication wish the sponsor, frequently the site will call someone at the sponsor. The content of many of these conversions may need to be noted in the study data.

The study protocol may require a CI/CRC to sign the CRF pages either before the CPA performs the source document verification, when the patient book is complete or both. The signature task can be made easier for the investigator site by telling them which CRFs are complete and need a signature, and when data on a signed CRF has changed and needs another signature. Additionally, the investigator sites need to know which CRFs they have examined and which ones they have not examined.

The management of drug inventory during a study is critical. A complete accounting of all study medication is required by the regulatory agencies. The investigator site needs to dispense study medication to their patients in the study and record this transaction. Additionally, when the sponsor issues study medication to the investigator site, this transaction and the receipt of the study medication by the investigation site must also be recorded.

Occasionally, the investigator site will need to break the study blind for a particular patient (for example, when a study patient becomes pregnant.) This is an important transaction and it must be noted in the study data.

There are four clinical review roles to be performed at he Clinical Research Organization (CRO) and/or sponsor. The Clinical Research Associate (CRA), Clinical Data Manager, Medical Monitor, and Clinical Project Manager review the data that is generated by the investigator sites for completeness and consistency.

The Clinical Research Associate reviews all of the data provided by the investigator sites, ensures that the sites are following the protocol and that all of the information in the medical record is completely and accurately represented in the study data. Typically, a CRA is responsible for monitoring a number of sites, and their audit role requires them to visit their sites. The CRA needs to know exactly what is happening at all of their sates so that they can effectively monitor the site's activities. The CRA sends summary reports to the project manager and others at the sponsor.

The Clinical Data Manager (CDM) prepares and maintains the clinical study database. The CDM is involved in the design of the study database, validation checks, and the design of the CRFs. The CDM also reviews the data in the database ensuring that the data is complete and consistent.

The Medical Monitor is often the designer of the study protocol and may be responsible for making any of the necessary changes to or deviations from the protocol once that study has begun. The Medical Monitor also reviews the study data looking for data anomalies and irregularities with respect to patient safety. Like the CRA, the Medical Monitor reviews the data in the CRFs and the communications with the sites. The Medical Monitor may respond to a query from a CRA. Finally, the Medical Monitor is immediately notified whenever a serious adverse event is recorded.

The Clinical Project Manager oversees the entire data collection process. They directly manage the activities of the CRAs and CDMs and at times they will examine the study data in detail. Together with the Medical Monitor, the Clinical Project Manager reviews the progress of the study and reports status to the senior management at the sponsor.

To monitor a site effectively, a data reviewer periodically reviews the data in the CRFs. If a value is missing, the validity of a value is questionable, or there is some other cause for concern, the data reviewer issues a query by attaching a question or comment to a question on the CRF.

Before a clinical database can be locked, members of the review team may be required to sign the patient CRF books. The signature task is simplified by indicating which CRFs are complete and need a signature, and which data on a signed CRF has changed and requires another signature. In addition, the data reviewer needs to know which CRFs have already been examined and which have not been examined.

Just as the site must on occasion communicate with the sponsor, the data reviewer muss communicate with a site. These communications may or may not be included in the study data. In addition, some messages are critical and investigator site personnel must see these messages before continuing.

Data reviewers need to communicate with each other. A CPA may have a question for the medical monitor, or the medical monitor may notice something that they would like the CPA to investigate. Unlike queries, these communications are not part of the study database.

Occasionally, one or more of the data reviewers will want to lock some or all of the patient's records so that interim statistical analysis can be performed. A preferred embodiment of the present invention provides a mechanism for locking the data at a patient level.

The Clinical Research Associate (CRA), has specific additional functions, as well. The CRA can view an investigator site's data and issue queries to the sites.

Periodically, the CRA visits a site, reviews all of the data in the original medical records (the source documents) and compares this with the information in the CRFs. This is known as source document verification. The CRA monitors a CRF at the question level, meaning that part of a CRF could be considered reviewed, but the rest will still need monitoring at a later time. In a preferred embodiment of the present invention, the CRA is automatically notified when any CRF is ready for review.

The CRA often does not have access to the primary study database and must work off-line. Therefore, during verification he site cannot change the data being reviewed until after the review is complete.

The CRA must manage the documents chat are provided by the site. These include any regulatory documents and any additional documents that are generated by the site that must be included with the study data. The CRA must notify the site when one of these documents is about to expire.

From time to time, the CRA issues a report about a site. For example, these reports are issued when a site has been qualified for the study, when a site initiates a trial, after the CRY has monitored some of the data at a site, and when a site finishes its last study patient.

The Clinical Data Manager (CDM) also has specific additional functions. During the course of a trial, the CDM may need to change one or more of the discrepancy checks in the system.

Typically, codes are entered not by the study coordinator (CRC) but rather by the CDM. If a CRC enters an adverse event or concomitant medication without coding the data, the CDM supplies the appropriate code in the database. In addition, the CDM carefully reviews all coding of adverse events and concomitant medications, making any changes that are necessary for consistency.

The Medical Monitor is notified whenever a serious adverse event is recorded. This notification occurs as quickly as possible to ensure the safety of the affected patient and all other patients in the study.

The sponsor will occasionally send information to all members of the study team and/or to all of the sites.

In addition, it is occasionally necessary for the Medical Monitor to change some part of the study protocol or CRFs. If the change affects patient safety, the protocol change must be reviewed by an Institutional Review Board at each site before it can be implemented. This leads to the possibility that two or more versions of the protocol could be active at different sites simultaneously.

On rare occasions the Medical Monitor allows a site to violate the study protocol. When this occurs, there must be a documented record of the deviation with the Medical Monitor's approval. Additionally, the Medical Monitor must note the justification for the deviation in the study data.

Occasionally, the Medical Monitor will need to break the study blind for a particular patient (for example, when a study patient becomes pregnant). This is an important transaction and it must be recorded in the study data.

The Clinical Project Manager will sometimes act as an individual contributor CRA or CDM.

There are two other roles in the system which do not fit into any of the other categories. They are the Pharmacist and the Database Manager. Many investigator sites will have their own pharmacy on site, or they will work with a local pharmacy. In either case, the Pharmacist must have access to the clinical trial data application.

The Database Manager is responsible for the security and reliability of the clinical study database. During the design of the trial, the Database Manager works with the CDM designing the implementation of the data model for the trial. At the end of the trial, the Database Manager is responsible for moving the data out of the study database and into a statistical analysis database.

From time to time, a pharmacist must review information about the study such as the study protocol, the study reference manual, a study newsletter, and a list of frequently asked questions. During the study, the pharmacist may need to communicate with the sponsor personnel. As the study progresses, the pharmacist may have a question or may notice something that would be of interest to the sponsor. Some of these communications must be included in the study data.

The management of drug inventory during a study is critical. A complete accounting of all study medication is required by the regulatory agencies. The site needs to dispense study medication to their patients in the study and record this transaction. In addition, when the sponsor issues study medication to the site, this transaction must also be recorded.

When the study is complete and the database is locked, the Database Manager must rove the study data into a statistical database. The database structures of the clinical database must support this conversion.

Figure 3:
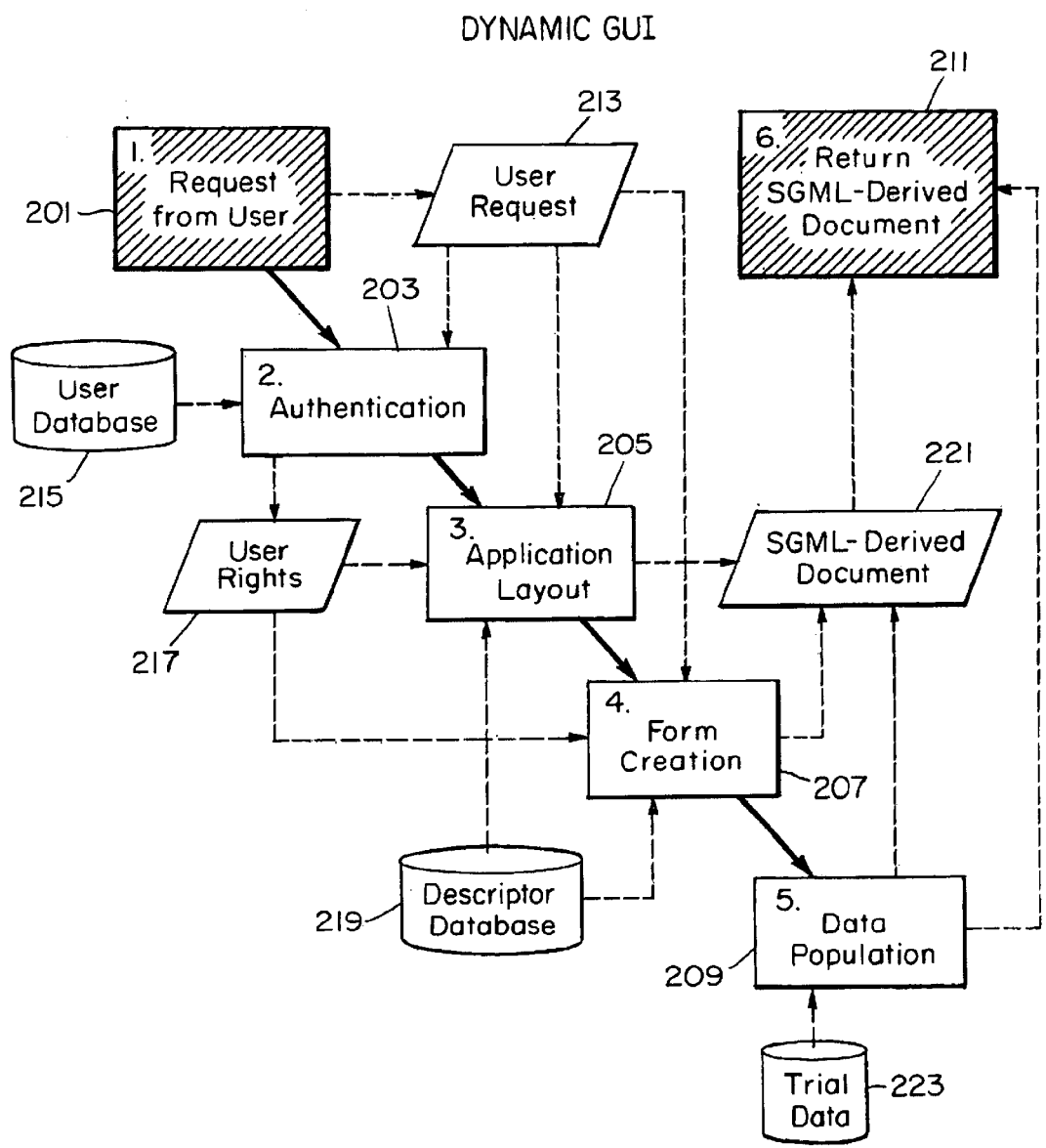
FIG. 3 is a block diagram illustrating she general flow of operation and data in the present invention.

FIG. 3 illustrates the general flow of operation and data in the present invention. While any Standard Generalized Markup Language (SGML)-derived language such as XML can be used, the preferred embodiment of the present invention utilizes Hypertext Markup Language (HTML). Rectangular boxes and solid bold lines indicate process flow, while dotted lines indicate data flow.

First, at 201, a request is received from a user, i.e., an investigative site, a sponsor site, a CRO site or a pharmacist. The request 213 is saved for later processing by any or all of the authentication process 203, the application layout process 205, or the form creation process 207.

Upon receipt of a request from a client, the authentication process 203 is invoked. A user database 215 is maintained, and the authentication process 203 checks user information contained in the request 213 against the user database 215. Such information may contain user identification, password, session information, valid time frame, etc., or other equivalent authentication means.

In addition to authenticating the user, the authentication process 203 examines toe user request 213 and checks with the user database 215 that the user is authorized to make such a request. The authentication process 203 can then establish which user rights 217 the user is to be given regarding the response to the particular request.

Once the requesting user has been authenticated, an application layout process 205 begins to construct the layout of the HTML response 221 to the client. This is a top layer describing what pieces are to be positioned within the HTML document and where. For example, this layer determines what the various frames should look like and what controls should appear therein. To make these decisions, the application layout process 205 relies on the original user request 213, the user rights 217 as determined previously by the authentication process 203, and descriptors maintained in a descriptor database 219.

Once he layout has been generated, the form creation process 207 uses .e user request 213 and descriptor database 219 to determine what questions, controls and other information should go into the form in the HTML document 221 previously laid out by the application layout process 205.

Next, the HTML document 221 is populated with clinical data by a data population routine, which retrieves the data from a trial database 223. The document 221 is now complete and ready for transmission back to the client (block 211).

Figure 4A:
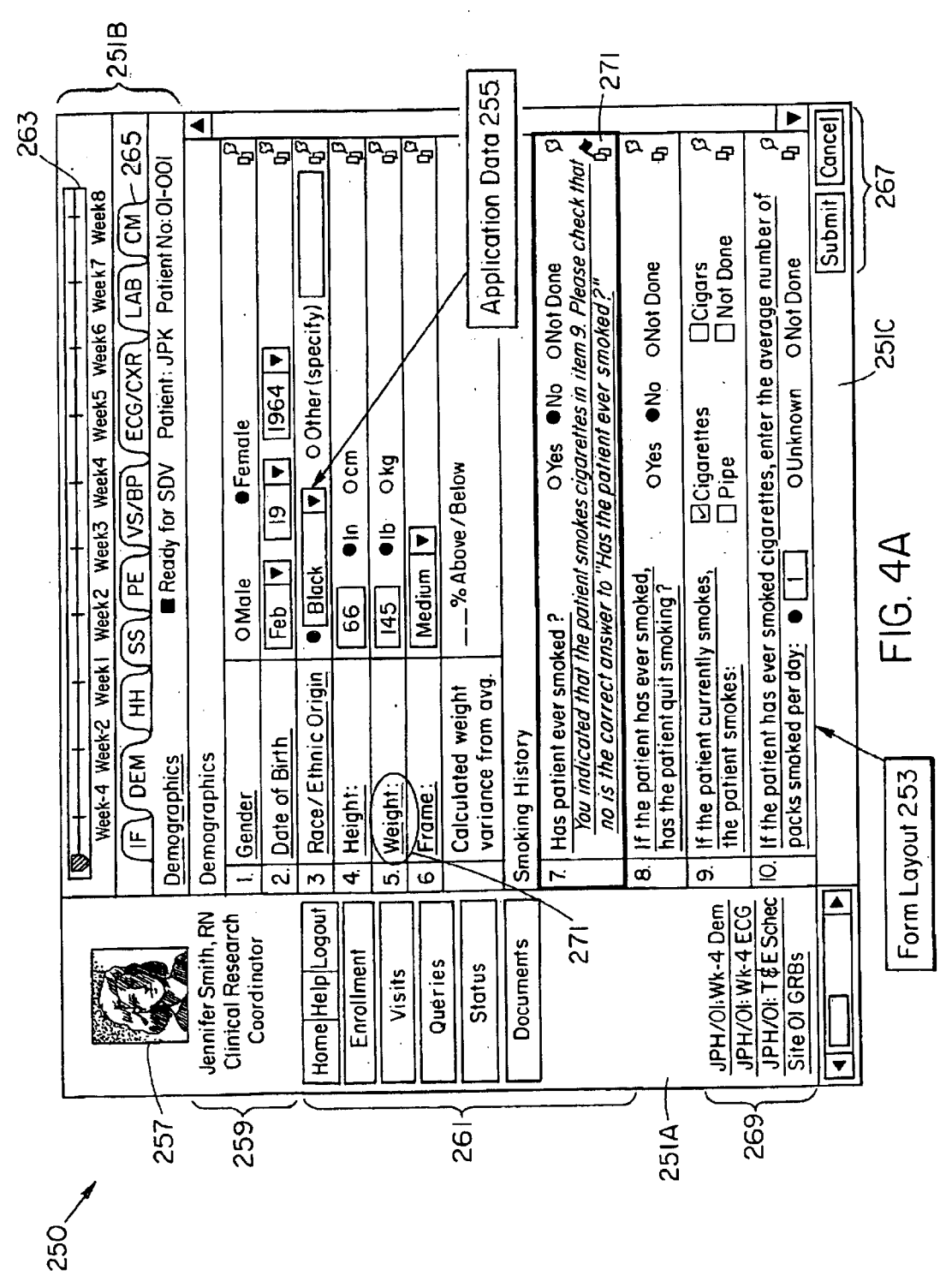

FIG. 4A illustrates a typical Web page 250 created by the present invention, as constructed from the HTML document 221 (from FIG. 3) when received and displayed by a client browser. Panels 251A–251C derive from the part of the HTML document 221 constructed by the application layout process 205 (FIG. 3), and contain various controls and other general information.

For example, panel 251A contains a photograph 257 of the person whose user identifier and password were used to first gain access to the system, or login. As discussed below, a preferred embodiment of the present invention displays this photograph 257 for the purpose or discouraging inadvertent use of the system by another person.

Other controls 261 are also provided in this panel 251A which permit the user to navigate to and examine various related documents and other information pages. Links 269 to recently accessed documents or data are also provided.

Panel 251B holds two additional controls: a time line control 263, and a file tab control 265. These are special types of controls which were necessitated by the present invention, yet are not easily implemented in a Web application. They are discussed below. Note however, that the time line control 263 is used to select a specific week (or some other unit of time) within the study, and that the file tab control 265 is used to select a particular form. Appearance of the form, of course, is dependent on the user's role, the protocol version and the week selected, as well as the actual form selected.

Finally, panel 251C holds controls 267 related to the form, here a Submit button and a Cancel button.

Once he panels 251A–251C are laid out by the application layout process 205, the selected form layout 253 is specified by the form creation process 207 (FIG. 3). In FIG. 4A, the "Demographics" form is displayed.

Figure 4C:
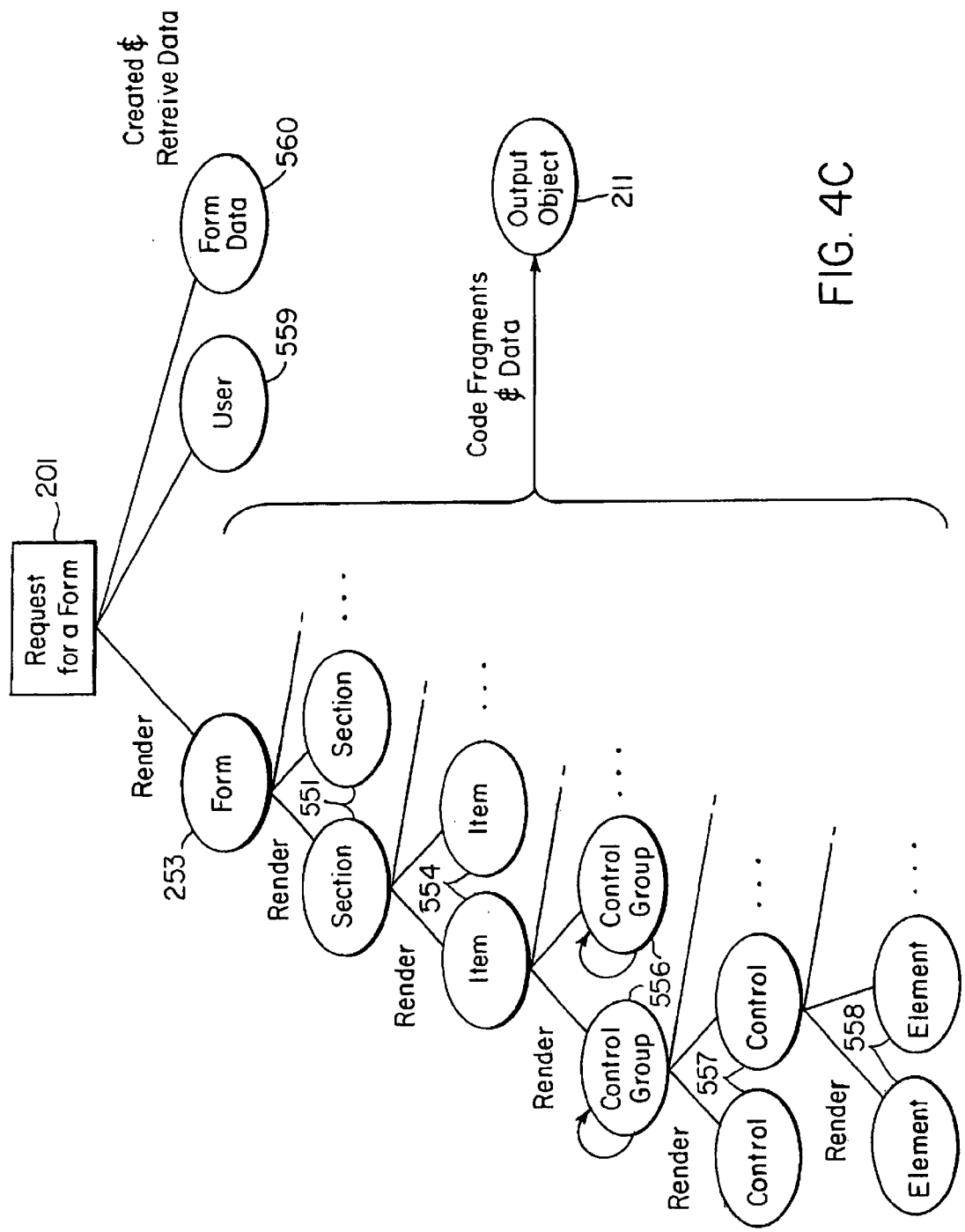

FIGS. 4B and 4C depict the hierarchical structure of an electronic CRF 253, also referred to simply as a form, of the present invention. The form 253 comprises one or more sections 551. Two sections 551 of the Demographics form 253 are visible: a Demographics section and a Smoking History section The remainder of the form can be brought into view by scrolling the scroll bar 553.

Each section comprises one or more items in which the user is typically asked to provide information about a patient, or of the information has already been provided, the information is displayed. For example, the Demographics section 551 has six items 554 numbered from 1 to 6, as well as a seventh item 555 in which a calculation is automatically performed by the system.

Each item 554 in turn may comprise one or more control groups 556. For example, item 2 ("Date of Birth") comprises control group 556, which in turn comprises three controls 557A–557C (generally 557 in FIG. 4C). Note that a control group may itself comprise control groups.

Each control may have one or more elements. For example, control 557A allows a user to select the patient's date of birth month. The twelve months are available in a list which is made visible by clicking on the arrow. Each month is an element 558 of the control 557A.

The significance of this hierarchy is that each of these hierarchical levels is treated as an object, with its own HTML fragments. As illustrated in FIG. 4C, when a user sends a request 201 for a specific form, the associated form object 253 is called up and passed user 559 and form 560 information. Form construction is begun by selecting certain HTML fragments. The form object 253 then determines from the trial database including information about the protocol version, and from user privileges and patient information, which sections are to be included, and those section objects are then called by the form object to render themselves.

As with the form object, each section object has its own HTML fragments, some of which are selected. This process continues, each object in the hierarchy selecting HTML fragments according to the user privileges, and calling its embedded objects.

Figure 4D:
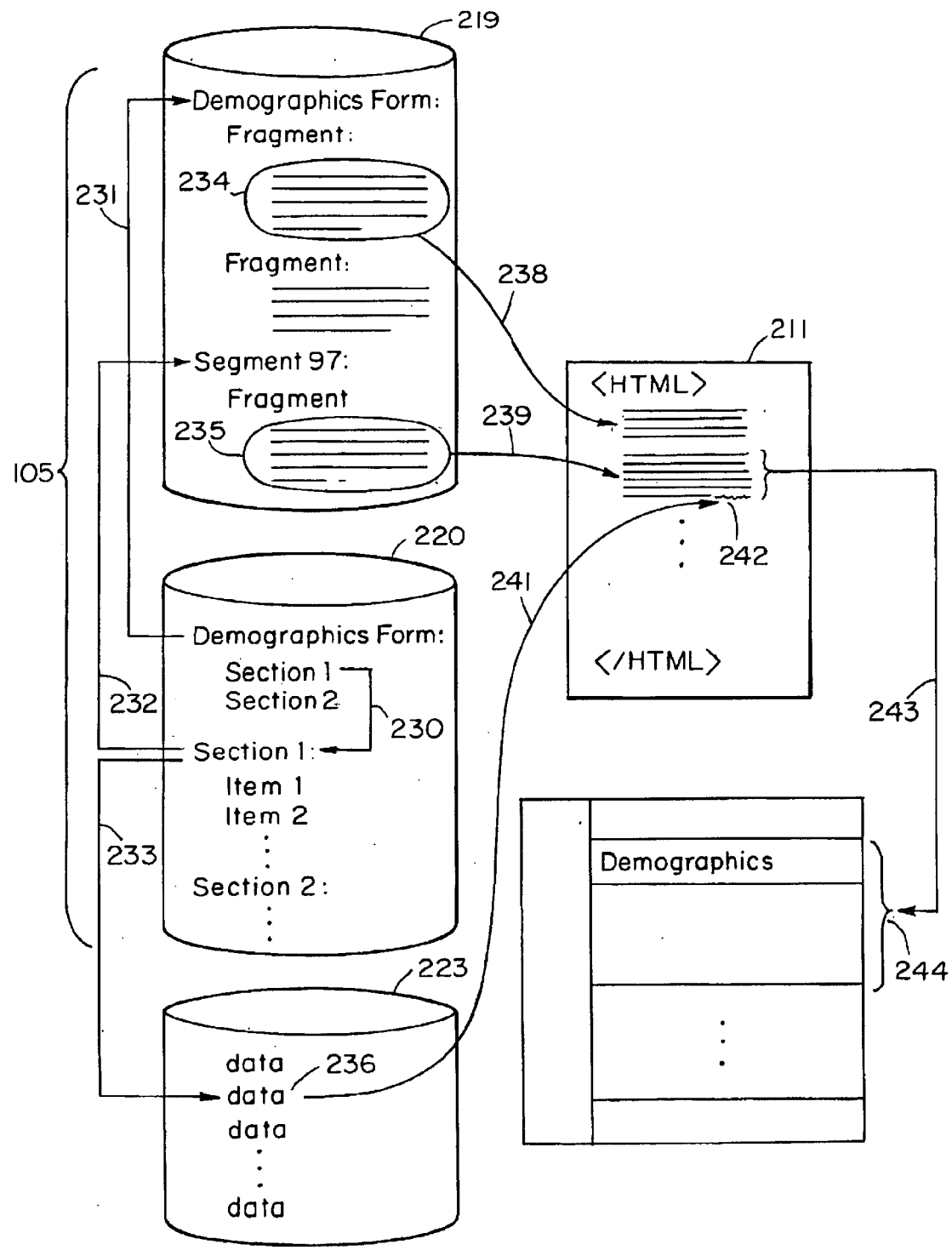
FIG. 4D is a schematic diagram illustrating the dynamic construction of a form template and the resulting document within the present invention.

FIG. 4D further illustrates how the HTML document 211 is constructed dynamically from fragment templates and from data. A trial database 220 stores structural information of the form object hierarchies as previously discussed. A descriptor database 219 is essentially a library of HTML code fragments. These two databases together make up the meta database 105. A clinical database 223 stores data collected during the trial.

For example, the Demographics Form is described as having two sections, Section 1 and Section 2. In the preferred embodiment, pointers are used, such as the pointer 230 to Section 1. Each section in turn has pointers to its items, and so on.

Each part of the hierarchy also points to corresponding code fragments in the descriptor database 219. For example, the high level Demographics form object comprises a pointer or identifier 231 which points to various code fragments 234. The object decides which fragments to use and which to reject, depending on user rights. The selected template fragment is copied (indicated by 238) into the document 211.

Each object in the hierarchy behaves similarly. Section 1 object data in the trial database 220 has a pointer 232 to its own corresponding code fragments in the descriptor database 219. Again, those code fragments or templates selected, such as code fragment 235, are copied into the document 211, as indicated by arrow 239.

In addition, the object for Section 1 also has a pointer 233 to data 236 stored in the clinical database 223 which is combined, in the output document 211, with the fragment template 235. The data 236 is copied, as indicated by arrow 241, into the document 211, and replaces some placeholder from the original fragment. The copied data is indicated by reference 242.

Finally, the output document 211 is sent, of published, to the requester, whose browser renders the form. Arrow 243 demonstrates now one of the section fragments with trial data is rendered into a section 204 of the form.

Of course, the clinical data is initially entered by the CI/CRC and stored in the trial database when submitted. Upon later retrieval for review or editing (assuming proper user rights), the stored data is filled in under the data population process 209 (FIG. 3), wherein individual control or element objects retrieve and display actual clinical data from the clinical database 223.

Note that while code fragments are generally in the form of HTML statements, they can also contain small scripted statements written in a language such as Javascript, which might be used to implement certain rules. For example, a rule might allow patient temperatures only within a certain range, to protect against the entering of Celsius temperatures instead of Fahrenheit. Checking with rules at the browser using a language such as Javascript obviates the extra transmissions back and forth that would be required if all checks were to be done at the server. Such rules may be based on the protocol which was active at the time certain data was entered.

In FIG. 4B, an inconsistency in the data has been found. The user has indicated in Question 7 that the patient has never smoked, yet in Question 9 has indicated that the patient smokes cigarettes. Thus a query 271 has been entered by a CRA asking for further verification and appears on the form for the user to respond to.

Finally, note that the text of each question is a link to additional information. For example, the text 271 of Question 5, "Weight" is a link to one of several documents explaining weight in the context of the protocol. This is discussed further below.

Figures 5, 6:
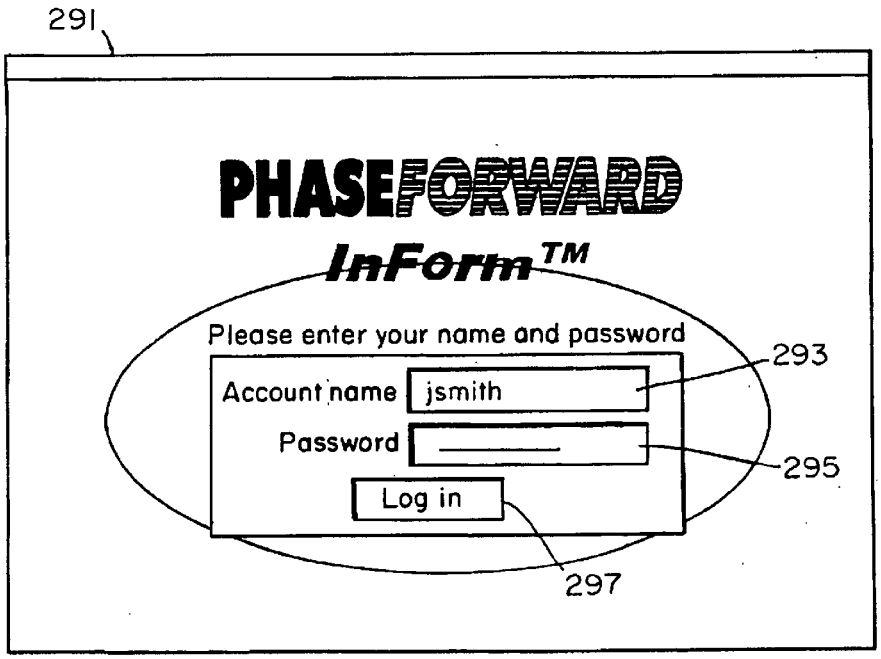
FIG. 5 is a diagram illustrating how the form of FIG. 4A might appear for a different user.
FIG. 6 is a diagram of a login screen.

FIG. 5 illustrates how, in the preferred embodiment, the same form can differ for a different user with a different role and therefore different access rights. Here, User2 is a Clinical Research Associate (CRA) with the Sponsor. The Sponsor is not allowed to enter or alter data. Thus patient data at 275 is simply displayed as text and is not editable. No controls are available.

Note also that for User2, different controls 277 are provided in the application layout panel 251A. Here, there are two additional controls: Signatures and Monitor, because these are CRA functions. Note also that because the form does not allow data entry, the controls in pane 251C are also different from those of FIGS. 4A and 4B.

Preventing Inadvertent Use

FIG. 6 illustrates a typical login screen of the present invention as displayed on a client browser. A user is asked to provide an account name 293 and a password 295. Upon clicking on the Log In button 297, the account name and password are transmitted over the Internet to the Web Server 101 (FIG. 2) where they are then submitted to the Application Server 103 for authentication. Alternatively, authentication could be performed using alternative methods such as a secure identification card, digital certificates or biometric characteristics.

A preferred embodiment of the present invention displays a photograph 257 (FIG. 4A) for the purpose of discouraging inadvertent use of the system by another person. For instance, if the person logged in happens to walk away for a break, take a telephone call, etc. and another user comes along and logs in using his own login, and this second user takes a break, while the first user returns, the first user will see instantly that she is no longer logged in. A photograph catches the attention or he user much more readily than would a text-only name.

In the preferred embodiment, the name and role 259 of the logged-in user are provided under the photograph 257. Thus, if the first user forgot to log out, a second user coming upon the system, and unfamiliar with the first user, could visually identify the first user, or, if unable to find the first user, because the name is provided, could look the first user up in a directory if it were necessary to contact the first user.

Integrated Dashboard

In a preferred embodiment, when the user has been authenticated, a "dashboard" 301 customized to the user is returned to the client browser and displayed.

Figure 7:
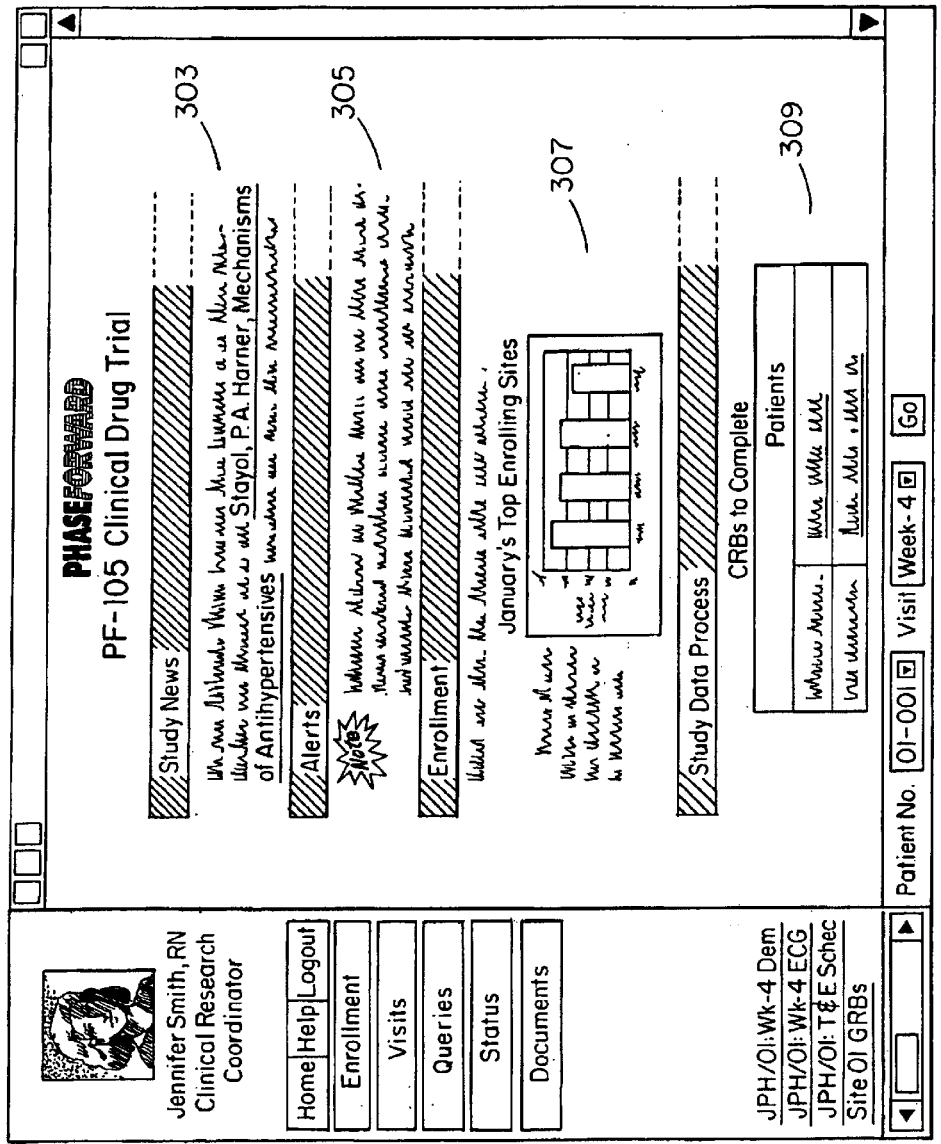
FIG. 7 is a diagram illustrating the dashboard screen of the present invention.

FIG. 7 is a diagram illustrating the dashboard screen of the present invention. The dashboard 301 contains various information and links regarding the study. For example, it contains study news 303 which the user should read and alerts 305 which may be critical. It also contains study progress graphs 307, a list of work to be completed 309 with navigational links, and additional information. It serves as a home base for the user.

Intermediate Frames

While frames with curved corners can be aesthetically pleasing, HTML frames do nor provide such curved borders. Thus one aspect of the present invention is the use of intermediate frames to provide the curves.

Figure 8:
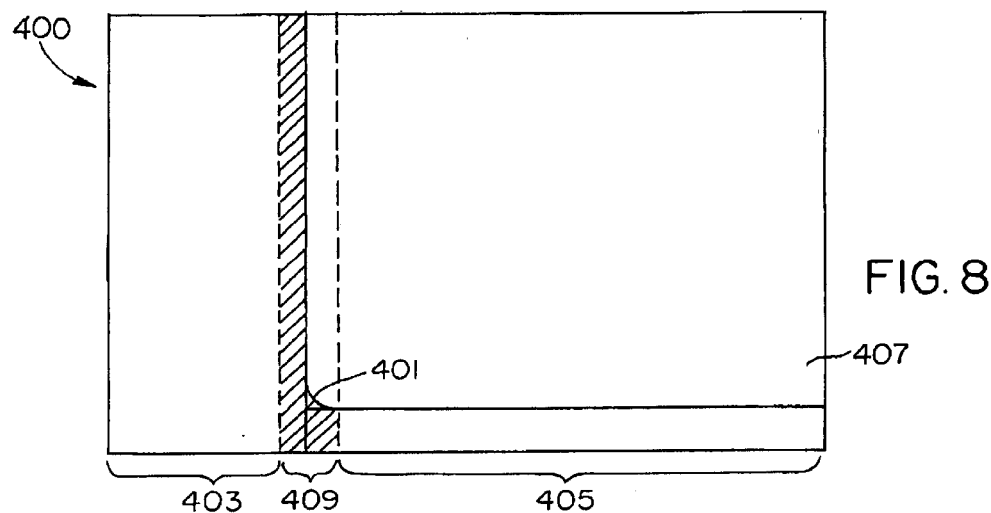
FIG. 8 is a diagram illustrating intermediate frames as used by the present invention.

FIG. 8 is a diagram illustrating the use of an intermediate frame by the present invention. Normally, a Web display may be broken down into several independent frames. Here, Web page 400 is divided functionally into three independent frames: a control panel frame 403, a content action panel frame 405 and a content panel frame 407.

The developer of the Web site washes to use a curved line 401 to visually differentiate the panels from each other. However, in HTML, frame borders are limited to horizontal and vertical lines.

A preferred embodiment of the present invention simulates curved or irregular shapes between frames by using an intermediate frame 409 between frames 403, 405 and 407 in which the curves and other frame borders are drawn. Thus, it appears to he user that the various panels actually have curved borders.

Bit Mapped Controls

As discussed earlier, in a preferred embodiment of the present invention, typical GUI controls which are normally executed in a stateful machine are implemented in a client browser. This is done in the preferred embodiment of the present invention by creating several bitmapped images which can be selectively placed such that the browser properly constructs the desired control. Bitmapped images may be formatted as gif, jpeg or other formats. Because browsers cache images locally, reuse of most of the bitmaps in multiple control elements results in rapid construction of the control element and thus the Web page.

One advantage of this approach is that because many of the images are reused, only one copy of each needs to be downloaded from the server. Second, labels are simple text and do not have associated images to be downloaded. The text is small and thus takes only a short time to transfer. Finally, because the image files corresponding to the bitmaps are locally cached by a browser, and because the image files are small, they consume only a small portion of memory.

Figure 9:
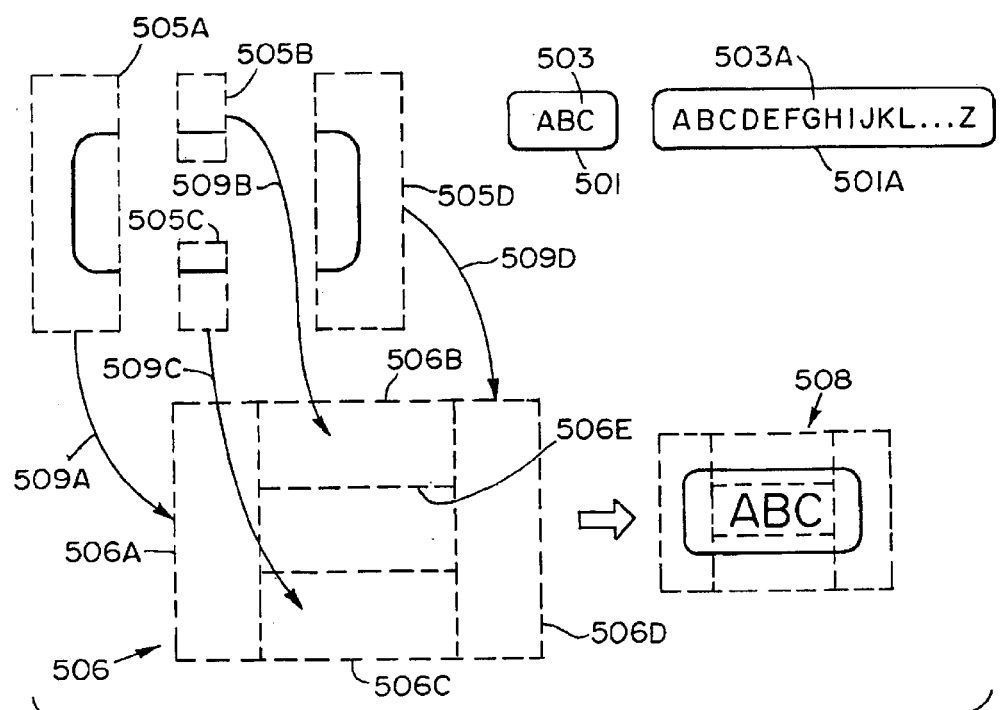
FIG. 9 is a diagram illustrating how a button control of the present invention comprises bit maps laid out in a table.

FIG. 9 illustrates this concept with a button control 501 containing the text label "ABC" 503. Ordinarily this entire button 501 is a single image. If many buttons are used, say having labels "DEF", "GHI" and so on, each must have a completely different image, each requiring its own initial transfer time and its own cache storage.

Instead, the present invention breaks the button image into several images 505A–505D. References or indications such as URLs to these images (which, in the preferred embodiment are generally "gif" files) are placed into a TABLE structure in an HTML document. Such a table 506 has five data entries, labeled 506A–506E. References to images 505A–505D are placed in four of the table entries 506A–506D, resulting in the placement by a browser, of the images in the table 506, as indicated by arrows 509A–509D respectively. The label text "ABC" is placed, with a background color matching the images 505A–505D, into the remaining table entry 506E.

Thus, while the application may use many different buttons, only the labels are different—the same images are reused by all of the buttons. No additional image files need to be transferred over the Internet. Only the text needs to be transferred and text takes but a fraction of the time an image takes to transfer. Since the images are reused, storage in the cache is much smaller as well.

Note also that an HTML-compatible browser automatically extends bitmapped images to fit a required space. Since a table adjusts itself to contain its data entries, a button 501A having a long label 503A (say the entire alphabet) would be drawn having a label space 506E long enough to contain the entire label. Table entries 506B and 506C would be lengthened accordingly, and therefore bitmapped images 505B and 505C would be extended to fill these lengthened entries, even though only minimal descriptions of the bitmaps is provided.

Below is sample HTML code to produce a button from several gif files. Bitmap images 505A–505D (FIG. 9) correspond to files named respectively "but_bot_left.gif", "but_bot_top.gif", "but_bot_right.gif", and "but_bot_bot.gif". The label of this particular button is "Go". Note also that each of the table entries has the text: HREF= "tabs.htm". Thus clicking anywhere on the button will cause the browser to request a Web page identified as "tabs.htm".

```
<HTML>
<!--//////////////////////////////////////////////////////  -->
<!--// Copyright © 1997–1998 Phase Forward Inc.   -->
<!--//    51 Winchester Street, Newton MA 02161   -->
<!--//           All Rights Reserved              -->
<!--//////////////////////////////////////////////////////  -->
<HEAD>
<STYLE>
TD
    {
        font-size: 8pt;
        font-family: Arial, "Sans Serif";
        text-align: center;
        vertical-align: middle;
        font-weight: bold;
        color: #CCCCCC;
    }
TD.menu
    {
        line-height: 10px;
        height: 8px;
    }
TD.TDLeft
    {
        text-align: left;
        vertical-align: middle;
    }
TD.TDRight
    {
        text-align: right;
        vertical-align: middle;
    }
A: link
    {
        color: #CCCCCC;
        font-size: 8pt;
        font-family: Arial, "Sans Serif";
        font-weight: bold;
        text-align: center;
        text-decoration: none;
    }
</STYLE>
</HEAD>
<BODY>
    <TD NOWRAP TITLE="Click here to go to the patient visit">
        <TABLE BORDER="0" CELLSPACING="0" CELLPADDING="0"
            VALIGN="middle" ALIGN="left">
            <TR>
                <TD ROWSPAN="3" NOWRAP><A HREF="tabs.htm"><IMG
                    SRC="./images/but_bot_left.gif"
                    BORDER="0"></A></TD>
                <TD NOWRAP><A HREF="tabs.htm"><IMG
                    SRC="./images/but_bot_top.gif" WIDTH="34"
                    HEIGHT="4" BORDER-"0"></A></TD>
                <TD ROWSPAN="3" NOWRAP><A HREF="tabs.htm"><IMG
                    SRC="./images/but_bot_right.gif"
                    BORDER="0"></A></TD>
            </TR>
            <TR>
                <TD CLASS="menu" BGCOLOR="#336699" NOWRAP><A
                    HREF="tabs.htm">Go</A></TD>
            </TR>
            <TR>
                <TD NOWRAP><A HREF="tabs.htm"><IMG
```

-continued

```
        SRC="./images/but_bot_bot.gif" WIDTH="34"
        HEIGHT="5" BORDER="0"></A></TD>
      </TR>
    </TABLE>
    </TD>
</BODY>
```

Note that in HTML, a table structure is delimited by the <TABLE> and </TABLE> tags. Each row begins with the tag <TR> and optionally ends with </TR>. Within each row, each column, or table data, begins with <TD> and optionally ends with </TD>. A COLSPAN=X or ROWSPAN=Y specification within a <TD> tag indicates that the corresponding entry is to span X columns or Y rows respectively.

Figure 10A:
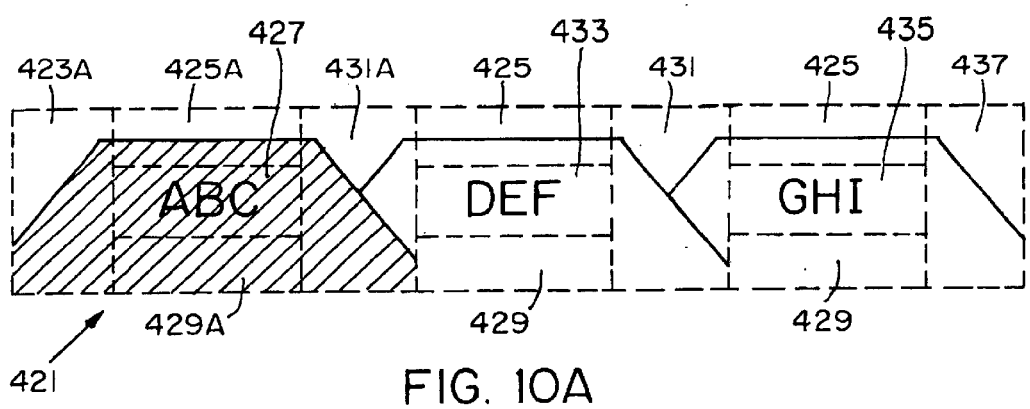
FIGS. 10A–10C are diagrams illustrating how the tab control of the present invention comprises bit maps laid out in a table.
Figure 10B:
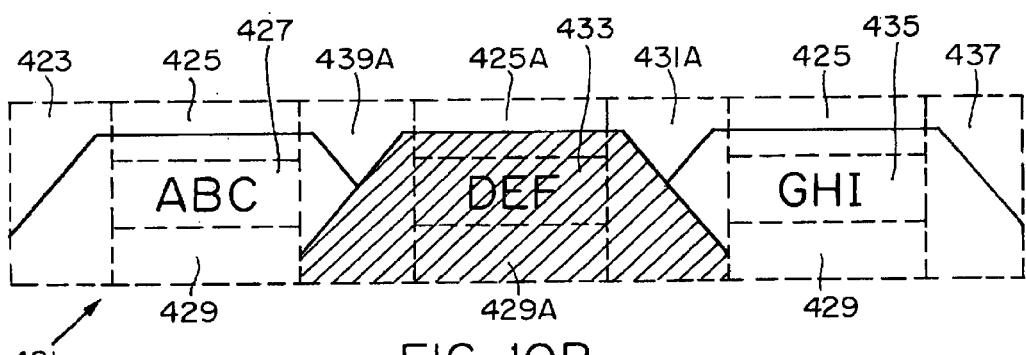
Figure 10C:
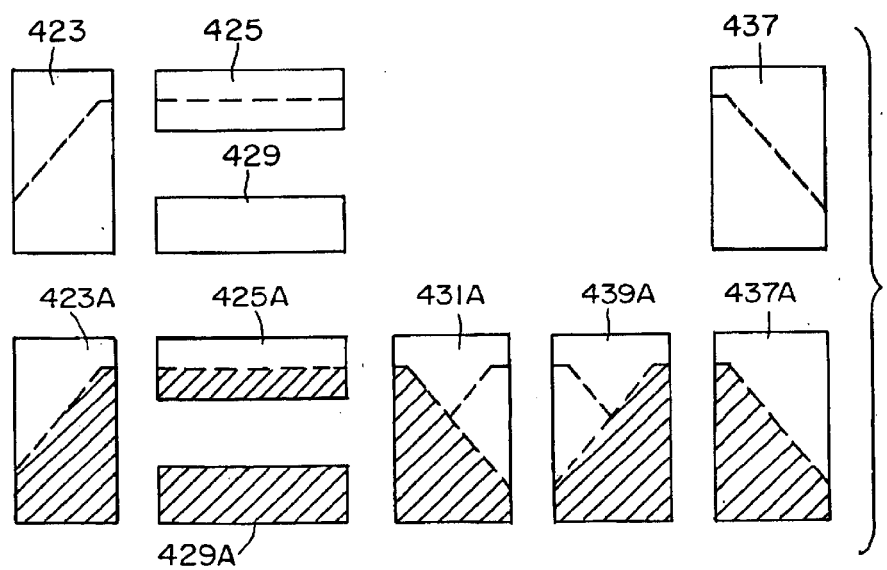

FIGS. 10A, 10B and 10C illustrate a file tab, or tab, control used by the present invention. FIG. 10A shows a tab control 421 having three tabs, although a tab control with any number of tabs can be implemented with this technique. As shown, the first tab element, labeled "ABC" is selected.

The tab control 421 is subdivided into many small sections, shown individually in FIG. 10C, each of which, except for label sections, has a corresponding image. As with the button control, many of the images are reused. Each image has a shaded version and an unshaded version. A tab is shaded if it has been selected. For example, a right piece bitmap 437, a top piece bitmap 425, and a bottom piece bitmap 429 define most of the third "GHI" tab. The label 435 is not a bitmap but rather, as with button labels described above, is simply text with a background color to match the surrounding bitmaps. Bitmap 431 is shared by the "GHI" tab and the adjacent "DEF" tab.

The "DEF" tab uses the same top and bottom piece bitmaps 425, 429. Therefore, these bitmaps will not have to be transferred again since they were gust transferred in order to draw them into the "GHI" tab. Of course, the "DEF" tab here uses a unique label ("DEF"), but since that is simple text, it is placed directly in the table structure and as a result there is no significant overhead in its transmittal. Another overlapping piece bitmap 431A is shared between the "DEF" tab and the selected "ABC" tab.

The "ABC" tab uses shaded left, top and bottom piece bitmaps 423A, 425A, 429A respectively, to show that the "ABC" tab is selected. The label "ABC" 427 is data embedded directly in the table data definition.

Each of these small bitmap images has a HREF element assigned to it, i.e. a reference to send to the server if the user clicks the mouse button on the bitmap. Although the same top bitmap 425 is used for multiple tabs, each realization of the bitmap may have a different HREF assignment. Thus, for example, when the user clicks anywhere within any of the top 425 or bottom 429 bitmaps or the label 427 associated with the "DEF" tab, information regarding "DEF" may be retrieved from the server and displayed on the browser. In addition, the tab control appearance must change to indicate that "DEF" has been selected.

Thus, the tab control now appears as shown in FIG. 10B. Only two new images are required: the shared bitmap 431A between the "ABC" and "DEF" tabs has been replaced by a bitmap 439A with a different overlapping appearance, and the leftmost piece 423A is no longer shaded and must be replaced with piece 423. These are the only piece of the tab control that need to be provided by the server.

As with the button discussed above, without this technique, it is necessary to download and cache the entire tab control in each of its three possible states, i.e. three bitmap of the entire tab control, each with a different tab selected. This requires much more cache memory than the present invention, as well as much more transmission time when the maps have not been cached (and each transmission is a transmission of the entire tab control bitmap.) The present invention, on the other hand, uses one small top bitmap 425 for each tab, as well as a bottom 429, left 423, and right 437 pieces, or their shaded versions 425A, 429A, 423A, 437A respectively, and right overlap 431A and left overlap 439A pieces all of which are significantly smaller than the whole. This difference becomes even more significant where the number of tabs is larger. As with the button control, the top and bottom tab bitmaps 425, 429 respectively can be extended and therefore the actual bitmaps are extremely small, just a few pixels wide and therefore consume a very small amount of cache memory.

Another advantage to the present invention is that if the form changes so that the tab control has additional tabs, no further bitmaps need to be transferred. All of the necessary bitmaps will have been cached. Only the table structure with text labels, tab selection information, and references to the bitmap files needs to be transferred.

Yet another advantage is that the present invention alleviates the need to create more images when a form changes. For example, in the prior art, if a tab control comprises seven individual tab control elements, seven different images must have been created—each one having a different tab selected. If it becomes necessary to add an eighth tab control element, eight new images must be created. In the present invention, no further images need to be created.

Preferably, these bitmaps are arranged by placing them in a table structure. For example, the code below defines an HTML table in which the positions and files containing the bitmaps are specified.

Also, in a preferred embodiment, the selected tab (whose associated form is displayed) is colored differently and rendered differently than the non-selected tabs. Thus there are different images for selected and non-selected tab parts. However, since a label is simply text and no image is used, a label's background color is specified within the corresponding table entree to match the tab. There is no image file to be transferred.

The following sample code produces a file tab control with five tabs labeled "VS", "LAB", "An", "CM", and "CMP" respectively, with "VS" indicated as the selected form.

```
<HTML>
<!--////////////////////////////////////////////////////////////  -->
<!--// Copyright © 1997-1998 Phase Forward Inc.   -->
<!--//    51 Winchester Street, Newton MA 02161   -->
<!--//           All Rights Reserved              -->
<!--////////////////////////////////////////////////////////////  -->
<HEAD>
<META HTTP-EQUIV="Content-Type" content="text/html;
charset=iso-8859-1">
<TITLE>Phase Forward Demo CRF Navigation Bar</TITLE>
<STYLE>
BODY
    {
        margin-top: 0px;
        margin-left: 0px;
        margin-right: 0px;
        margin-bottom: 0px;
    }
TD
    {
        vertical-align: bottom;
    }
TD.tabselect
    {
        color: #FFFF00;
        font-size: 10pt;
        font-family: Arial, "Sans Serif";
        font-weight: bold;
        text-align: center;
        vertical-align: center;
        line-height: 8pt;
        height: 11pt;
    }
TD.tabnotselect
    {
        color: #CCCCCC;
        font-size: 10pt;
        font-family: Arial, "Sans Serif";
        font-weight: bold;
        text-align: center;
        vertical-align: center;
        line-height: 8pt;
        height: 11pt;
    }
A:link
    {
        color: #CCCCCC;
        font-size: 10pt;
        font-family: Arial, "Sans Serif";
        font-weight: bold;
        text-decoration: none;
        text-align: center;
    }
A:visited
    {
        color: #CCCCCC;
        font-size: 10pt;
        font-family: Arial, "Sans Serif";
        font-weight: bold;
        text-decoration: none;
        text-align: center;
    }
A:hover
    {
        color: #FFFFCC;
    }
</STYLE>
</HEAD>
<BODY BGCOLOR="#666666">
    <MAP NAME="OffMidMap1">
        <AREA SHAPE="poly" HREF="tab_vsbp.htm"
            COORDS="0,1,4,1,10,6,15,20,15,24,0,24" TITLE="Vital
            Signs/Blood Pressure">
        <AREA SHAPE="poly" HREF="tab_lab.htm"
            COORDS="27,1,22,1,17,6,14,10,17,20,17,24,27,24,"
            TITLE="Laboratory">
    </MAP>
    <MAP NAME="OnMidLMap2">
        <AREA SHAPE="poly" HREF="tab_lab.htm"
```

-continued

```
         COORDS="0,1,4,1,10,6,15,20,15,24,0,24"
         TITLE="Laboratory">
   </MAP>
   <MAP NAME="OnMidRMap3">
      <AREA SHAPE="poly" HREF="tab_cm.htm"
         COORDS="27,1,22,1,17,6,14,10,17,20,17,24,27,24,"
         TITLE="Concomitant Medications">
   </MAP>
   <MAP NAME="OffMidMap4">
      <AREA SHAPE="poly" HREF="tab_cm.htm"
         COORDS="0,1,4,1,10,6,15,20,15,24,0,24"
         TITLE="Concomitant Medications">
      <AREA SHAPE="poly" HREF="tab_cmp.htm"
         COORDS="27,1,22,1,17,6,14,10,17,20,17,24,27,24,"
         TITLE="Study Compliance">
   </MAP>
<TABLE BORDER="0" CELLPADDING="0" CELLSPACING="0"
HEIGHT="100%">
   <TR>
      <TD VALIGN="bottom"><TABLE BORDER="0" CELLPADDING="0"
         CELLSPACING="0" ALIGN="left">
         <TR>
            <TD ROWSPAN="3" NOWRAP><A
               HREF="tab_vsbp.htm"><IMG
               SRC="./images/tab_off_l.gif" BORDER="0"
               ALT="Vital Signs/Blood Pressure"></A></TD>
            <TD NOWRAP><A HREF="tab_vsbp.htm"><IMG
               SRC="./images/tab_off_top.gif" BORDER="0"
               WIDTH="52px" HEIGHT="5" ALT="Vital Signs/Blood
               Pressure"></A></TD>
            <TD ROWSPAN="3" NOWRAP><IMG
               SRC="./images/tab_off_mid.gif" BORDER="0"
               USEMAP="#OffMidMap1"></TD>
            <TD NOWRAP><A HREF="tab_lab.htm"><IMG
               SRC="./images/tab_off_top.gif" BORDER="0"
               WIDTH="40px" HEIGHT="5"
               ALT="Laboratory"></A></TD>
            <TD ROWSPAN="3" NOWRAP><IMG
               SRC="./images/tab_on_midl.gif" BORDER="0"
               USEMAP="#OnMidLMap2"></TD>
            <TD NOWRAP><IMG SRC="./images/tab_on_top.gif"
               BORDER="0" WIDTH="32px" HEIGHT="5"
               ALT="Adverse Experiences"></TD>
            <TD ROWSPAN="3" NOWRAP><IMG
               SRC="./images/tab_on_midr.gif" BORDER="0"
               USEMAP="#OnMidRMap3"></TD>
            <TD NOWRAP><A HREF="tab_cm.htm"><IMG
               SRC="./images/tab_off_top.gif" BORDER="0"
               WIDTH="34px" HEIGHT="5" ALT="Concomitant
               Medications"></A></TD>
            <TD ROWSPAN="3" NOWRAP><IMG
               SRC="./images/tab_off_mid.gif" BORDER="0"
               USEMAP="#OffMidMap4"</TD>
            <TD NOWRAP><A HREF="tab_cmp.htm"><IMG
               SRC="./images/tab_off_top.gif" BORDER="0"
               WIDTH="43px" HEIGHT="5" ALT-"Study
               Compliance"></A></TD>
            <TD ROWSPAN="3" NOWRAP><A HREF="tab_cmp.htm"><IMG
               SRC="./images/tab_off_r.gif" BORDER="0"
               ALT="Study Compliance"></A></TD>
         </TR>
         <TR>
            <TD CLASS="tabnotselect" BGCOLOR="#336699"
               NOWRAP><A HREF="tab_vsbp.htm" TITLE="Vital
               Signs/Blood Pressure" >VS/BP</A></TD>
            <TD CLASS="tabnotselect" BGCOLOR="#336699"
               NOWRAP><A HREF="tab_lab.htm"
               TITLE="Laboratory">LAB</A></TD>
            <TD CLASS="tabselect" BGCOLOR="#003366"
               TITLE="Adverse Experiences" NOWRAP>AE</TD>
            <TD CLASS="tabnotselect" BGCOLOR="#336699"
               NOWRAP><A HREF="tab_cm.htm" TITLE="Concomitant
               Medications">CM</A></TD>
            <TD CLASS="tabnotselect" BGCOLOR="#336699"
               NOWRAP><A HREF="tab_cmp.htm" TITLE="Study
               Compliance">CMP</A></TD>
         </TR>
         <TR>
            <TD BGCOLOR="#336699" NOWRAP><A
```

-continued

```
           HREF="tab_vsbp.htm"><IMG
           SRC="./images/tab_off_bot.gif" BORDER="0"
           WIDTH="52px" HEIGHT="5" ALT="Vital Signs/Blood
           Pressure"></A></TD>
         <TD BGCOLOR="#336699" NOWRAP><A
           HREF="tab_lab.htm"><IMG
           SRC="./images/tab_off_bot.gif" BORDER="0"
           WIDTH="40px" HEIGHT="5"
           ALT="Laboratory"></A></TD>
         <TD BGCOLOR="#003366" NOWRAP><IMG
           SRC="./images/tab_on_bot.gif" BORDER="0"
           WIDTH="32px" HEIGHT="5" ALT="Adverse
           Experiences"></TD>
         <TD BGCOLOR="#336699" NOWRAP><A
           HREF="tab_cm.htm"><IMG
           SRC="./images/tab_off_bot.gif" BORDER="0"
           WIDTH="34px" HEIGHT="5" ALT="Concomitant
           Medications"></A></TD>
         <TD BGCOLOR="#336699" NOWRAP><A
           HREF="tab_cmp.htm"><IMG
           SRC="./images/tab_off_bot.gif" BORDER="0"
           WIDTH="43px" HEIGHT="5" ALT="Study
           Compliance"></A></TD>
         <TD VALIGN="bottom" COLSPAN="3" NOWRAP><IMG
           SRC="./images/tab_off_bot.gif" WIDTH="1000"
           HEIGHT="5" BORDER="0"></TD>
       </TR>
     </TABLE></TD>
   </TR>
</TABLE>
</BODY>
</HTML>
```

The correlation between bitmaps from FIG. 10C and their corresponding file names is given in the table below:

| FIG. 10C ref. number | Filename in HTML code |
|---|---|
| 423A/423 | tab_on_l.gif/tab_off_l.gif |
| 425A/425 | tab_on_top.gif/tab_off_top.gif |
| 429A/429 | tab_on_bot.gif/tab_off_bot.gif |
| 431A | tab_on_midr.gif |
| 439A | tab_on_midl.gif |
| 437A/437 | tab_on_r.gif/tab_off_r.gif |

Figure 11A:
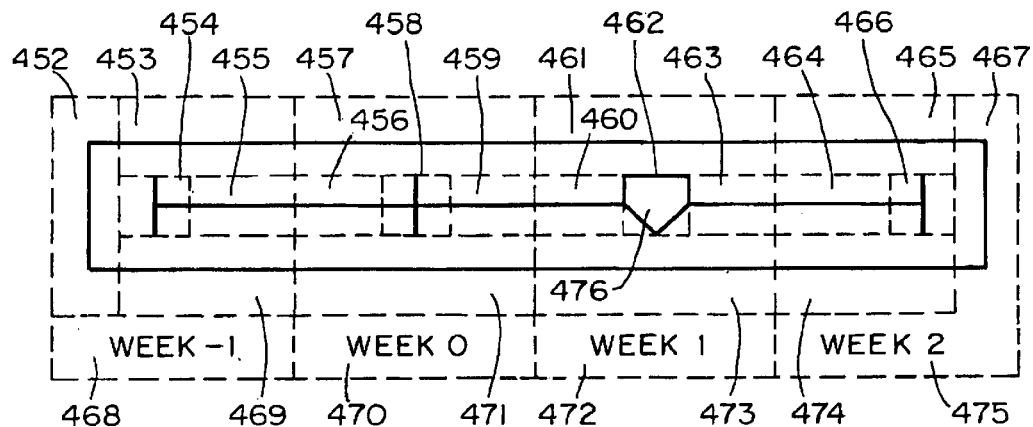
FIGS. 11A–11D are diagrams illustrating a linear control of the present invention.
Figure 11B:
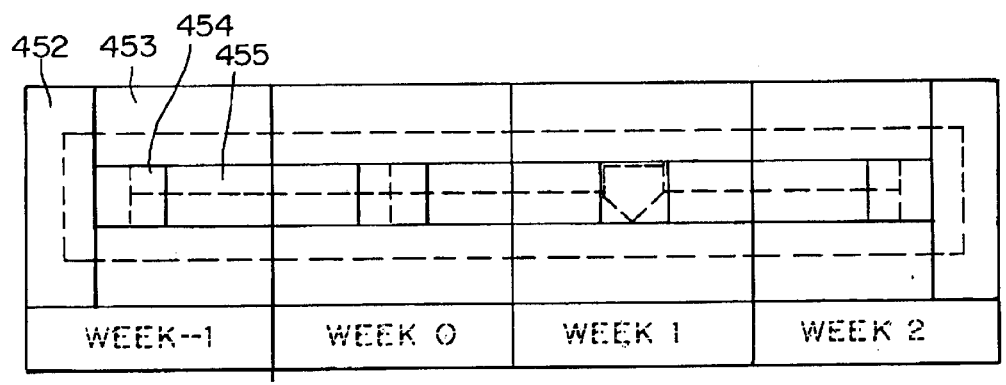
Figure 11C:
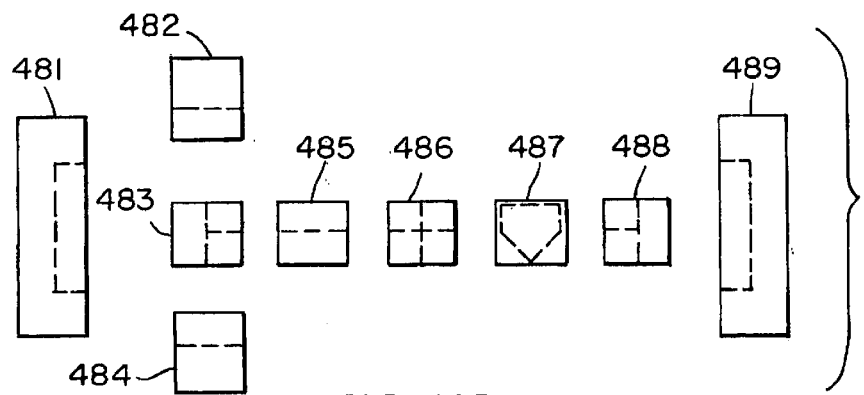

Similarly, FIGS. 11A, 11B and 11C illustrate a linear control, preferably a time-line control, of the present invention using the same technique. FIG. 11C shows the various bitmaps that are placed in a table structure to compose a linear control. The dashed lines show the outline of the bitmap, while the solid lines represent what is actually seen. Of course, color and shading can be used to produce a more dramatic effect, and in fact are used in the preferred embodiment.

Bitmap 481 defines the left end of the control and shows the left end of a frame which encloses the control. Similarly bitmaps 482, 483 and 489 define top, bottom and right frame pieces respectively of the control enclosure. Note that by defining a bitmap to span multiple rows or columns within a table entry does not change the appearance of the bitmap except to extend it in the vertical or horizontal direction respectively.

Bitmaps 483, and 485–488 define the various parts of the linear control itself. Bitmaps 483 and 488 are the left and right pieces respectively of the control and in the preferred embodiment are only used once per control. Bitmap 485 is the line part of the control and is used simultaneously in several places. Bitmap 486 has a continuation of the control line, plus a vertical tick. Bitmap 487 is used to show which value has been selected.

These bitmaps 481–489 can be assembled in various combinations to create linear controls of any size, and to show any control in any particular state. For example, in FIG. 11A, bitmaps 481–489 (from FIG. 11C) have been assembled into a table 451 to create a linear control with four stops. In addition, labels have been placed in the table below each stop. These labels are merely text entries with a background color matching the control, so that there is negligible overhead in obtaining the labels.

The following HTML code produces the linear control of FIG. 11A.

```
<HTML>
<!--////////////////////////////////////////////////////////  -->
<!--// Copyright © 1997–1998 Phase Forward Inc.   -->
<!--//    51 Winchester Street, Newton MA 02161   -->
<!--//            All Rights Reserved             -->
<!--////////////////////////////////////////////////////////  -->
<HEAD>
<META HTTP-EQUIV="Content-Type" content="text/html;
charset=iso-8859-1">
```

-continued

```
<TITLE>Phase Forward Demo Visit Bar</TITLE>
<STYLE>
BODY
    {
    margin-left: 0px;
    margin-top: 0px;
    }
TD
    {
    font-size: 8pt;
    font-family: Arial, "Sans Serif";
    font-weight: bold;
    text-align: center;
    vertical-align: middle;
    }
TD.tdselect
    {
    color: #FFFF00;
    }
A:link
    {
    color: #CCCCCC;
    font-size: 8pt;
    font-family: Arial, "Sans Serif";
    font-weight: bold;
    text-decoration: none;
    text-align: center;
    vertical-align: middle;
    line-height: 11px;
    height: 8px;
    }
A:visited
    {
    color: #CCCCCC;
    font-size: 8pt;
    font-family: Arial, "Sans Serif";
    font-weight: bold;
    text-decoration: none;
    text-align: center;
    vertical-align: middle;
    line-height: 11px;
    height: 8px;
    }
A:hover
    {
    color: #FFFFCC;
    }
TD.tickmark
    {
    vertical-align: middle;
    /*line-height: 12px;
    height: 12px;*/
    }
</STYLE>
</HEAD>
<BODY BGCOLOR="336699">
<TABLE BORDER="0" CELLPADDING="0" CELLSPACING="0"
HEIGHT="100%" ALIGN="left" VALIGN="top">
    <TR>
        <TD ROWSPAN="3"><IMG SRC="./images/tick_indent_l.gif"
            BORDER="0"></TD>
        <TD COLSPAN="2"><IMG
            SRC="./images/tick_indent_top.gif" BORDER="0"
            WIDTH="53" HEIGHT="5"></TD>
        <TD COLSPAN="3"><IMG
            SRC="./images/tick_indent_top.gif" BORDER="0"
            WIDTH="70" HEIGHT="5"></TD>
        <TD COLSPAN="3"><IMG
            SRC="./images/tick_indent_top.gif" BORDER="0"
            WIDTH="70" HEIGHT="5"></TD>
        <TD COLSPAN="3"><IMG
            SRC="./images/tick_indent_top.gif" BORDER="0"
            WIDTH="70" HEIGHT="5"></TD>
        <TD COLSPAN="3"><IMG
            SRC="./images/tick_indent_top.gif" BORDER="0"
            WIDTH="70" HEIGHT="5"></TD>
        <TD COLSPAN="3"><IMG
            SRC="./images/tick_indent_top.gif" BORDER="0"
            WIDTH="70" HEIGHT="5"></TD>
```

-continued

```
    <TD COLSPAN="3"><IMG
      SRC="./images/tick_indent_top.gif" BORDER="0"
      WIDTH="70" HEIGHT="5"></TD>
    <TD COLSPAN="2"><IMG
      SRC="./images/tick_indent_top.gif" BORDER="0"
      WIDTH="46" HEIGHT="5"></TD>
    <TD ROWSPAN="3"><IMG SRC="./images/tick_indent_r.gif"
      BORDER="0"></TD>
  </TR>
  <TR>
    <TD CLASS="tickmark"><A HREF="tl_wk-4.htm"
      TITLE=" "><IMG SRC="./images/tick_left.gif"
      BORDER="0"></A></TD>
    <TD CLASS="tickmark"><IMG SRC="./images/tick_line.gif"
      BORDER="0" WIDTH="35" HEIGHT="3"></TD>
    <TD CLASS="tickmark"><IMG SRC="./images/tick_line.gif"
      BORDER="0" WIDTH="26" HEIGHT="3"></TD>
    <TD CLASS="tickmark"><A HREF="tl_wk-2.htm"
      TITLE=" "><IMG SRC="./images/tick_middle.gif"
      BORDER="0"></A></TD>
    <TD CLASS="tickmark"><IMG SRC="./images/tick_line.gif"
      BORDER="0" WIDTH="26" HEIGHT="3"></TD>
    <TD CLASS="tickmark"><IMG SRC="./images/tick_line.gif"
      BORDER="0" WIDTH="26" HEIGHT="3" ></TD>
    <TD CLASS="tickmark"><A HREF="tl_wk0.htm"
      TITLE=" "><IMG SRC="./images/tick_middle.gif"
      BORDER="0"></A></TD>
    <TD CLASS="tickmark"><IMG SRC="./images/tick_line.gif"
      BORDER="0" WIDTH="26" HEIGHT="3"></TD>
    <TD CLASS="tickmark"><IMG SRC="./images/tick_line.gif"
      BORDER="0" WIDTH="26" HEIGHT="3"></TD>
    <TD CLASS="tickmark"><A HREF="tl_wk1.htm"
      TITLE=" "><IMG SRC="./images/tick_line.gif"
      BORDER="0"></A></TD>
    <TD CLASS="tickmark"><IMG SRC="./images/tick_line.gif"
      BORDER="0" WIDTH="26" HEIGHT="3"></TD>
    <TD CLASS="tickmark"><IMG SRC="./images/tick_line.gif"
      BORDER="0" WIDTH="26" HEIGHT="3"></TD>
    <TD CLASS="tickmark"><IMG
      SRC="./images/tick_middle_selected.gif"
      BORDER="0"></TD>
    <TD CLASS="tickmark"><IMG SRC="./images/tick_line.gif"
      BORDER="0" WIDTH="26" HEIGHT="3"></TD>
    <TD CLASS="tickmark"><IMG SRC="./images/tick_line.gif"
      BORDER="0" WIDTH="26" HEIGHT="3"></TD>
    <TD CLASS="tickmark"><A HREF="tl_wk4.htm"
      TITLE=" "><IMG SRC="./images/tick_middle.gif"
      BORDER="0"></A></TD>
    <TD CLASS="tickmark"><IMG SRC="./images/tick_line.gif"
      BORDER="0" WIDTH="26" HEIGHT="3"></TD>
    <TD CLASS="tickmark"><IMG SRC="./images/tick_line.gif"
      BORDER="0" WIDTH="26" HEIGHT="3"></TD>
    <TD CLASS="tickmark"><A HREF="tl_wk5.htm"
      TITLE=" "><IMG SRC="./images/tick_middle.gif"
      BORDER="0"></A></TD>
    <TD CLASS="tickmark"><IMG SRC="./images/tick_line.gif"
      BORDER="0" WIDTH="26" HEIGHT="3"></TD>
    <TD CLASS="tickmark"><IMG SRC="./images/tick_line.gif"
      BORDER="0" WIDTH="28" HEIGHT="3"></TD>
    <TD CLASS="tickmark"><A HREF="tl_wk8.htm"
      TITLE=" "><IMG SRC="./images/tick_right.gif"
      BORDER="0"></A></TD>
  </TR>
  <TR>
    <TD COLSPAN="2"><IMG
      SRC="./images/tick_indent_bot.gif" BORDER="0"
      WIDTH="53" HEIGHT="5"></TD>
    <TD COLSPAN="3"><IMG
      SRC="./images/tick_indent_bot.gif" BORDER="0"
      WIDTH="70" HEIGHT="5"></TD>
    <TD COLSPAN="3"><IMG
      SRC="./images/tick_indent_bot.gif" BORDER="0"
      WIDTH="70" HEIGHT="5"></TD>
    <TD COLSPAN="3"><IMG
    SRC="./images/tick_indent_bot.gif" BORDER="0"
    WIDTH="70" HEIGHT="5"></TD>
    <TD COLSPAN="3"><IMG
      SRC="./images/tick_indent_bot.gif" BORDER="0"
      WIDTH="70" HEIGHT="5"></TD>
```

-continued

```
    <TD COLSPAN="3"><IMG
        SRC="./images/tick_indent_bot.gif" BORDER="0"
        WIDTH="70" HEIGHT="5"></TD>
    <TD COLSPAN="3"><IMG
        SRC="./images/tick_indent_bot.gif" BORDER="0"
        WIDTH="70" HEIGHT="5"></TD>
    <TD COLSPAN="2"><IMG
        SRC="./images/tick_indent_bot.gif" BORDER="0"
        WIDTH="46" HEIGHT="5"></TD>
  </TR>
  <TR>
    <TD COLSPAN="3" STYLE='text-align:left'
        BGCOLOR="#336699" NOWRAP><A HREF="tl_wk-4.htm"
        TITLE="Placebo Run-In Visit 1"> Week
        – 4</A></TD>
    <TD COLSPAN="3" BGCOLOR="#336699" NOWRAP><A
        HREF="tl_wk-2.htm" TITLE="Placebo Run-In Visit
        2">Week –2</A></TD>
    <TD COLSPAN="3" BGCOLOR="#336699" NOWRAP><A
        HREF="tl_wk0.htm" TITLE="Baseline Visit">Week
        0</A></TD>
    <TD COLSPAN="3" BGCOLOR="#336699" NOWRAP><A
        HREF="tl_wk1.htm" TITLE="Treatment Visit 1">Week
        1</A></TD>
    <TD COLSPAN="3" CLASS="tdselect" BGCOLOR="#336699"
        TITLE="Treatment Visit 2" NOWRAP>Week 2</TD>
    <TD COLSPAN="3" BGCOLOR="#336699" NOWRAP><A
        HREF="tl_wk4.htm" TITLE="Treatment Visit 3">Week
        4</A></TD>
    <TD COLSPAN="3" BGCOLOR="#336699" NOWRAP><A
        HREF="tl_wk5.htm" TITLE="Treatment Visit 4
        (Optional)">Week 5</A></TD>
    <TD COLSPAN="3" STYLE='text-align:right'
        BGCOLOR="#336699" NOWRAP><A HREF="tl_wk8.htm"
        TITLE="Final Visit">Week 8</A></TD>
  </TR>
</TABLE>
</BODY>
</HTML>
```

Note in addition that certain table entries have anchors, denoted by the <A></A> element pair. An HREF specification within an <A> element specifies the source of a document of image file. Those parts of the control corresponding to table entries having anchors with HREF specifications will cause a message to be sent to the server when a user clicks in the entry area, requesting the specified document. The server processes that request, returning pertinent information about the selected week in the form, and at the same time, resending the table with the references to the image files reordered so that the control will appear with the user's selection selected and with a form appropriate for a particular visit. Thus the control appears to work as the user would normally expect, yet all of the work is done at the server. In addition, none (or at most one) of the bitmaps need to be downloaded because they have already been used and should be cached at the browser. Thus the transmission from server to client will not be hampered by a need to download many bitmaps.

Without the present invention, it is necessary to download from the server a very large bitmap comprising the entire control in a particular state, say with the first tab selected. For each state having a different tab selected, a separate, large bitmap of the entire tab control must be sent from the server if not already cached, and when these large bitmaps are cached, each consumes a very large amount of available cache memory.

Figure 11D:
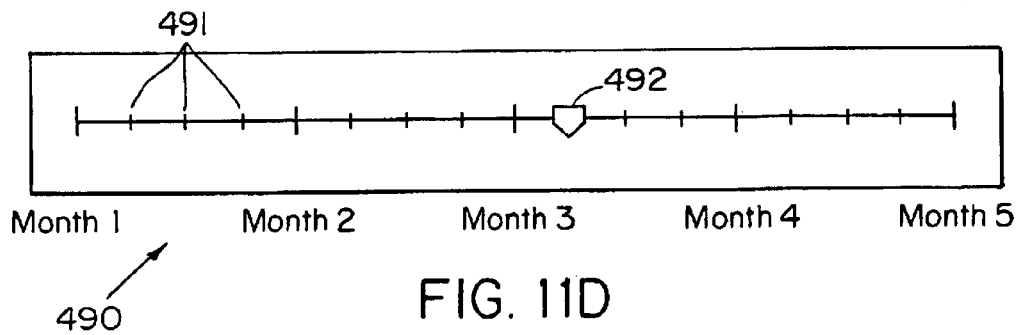

FIG. 11D illustrates a variation of the time-line control 490 in which the time-line is further subdivided with small ticks 491 which do not have their own associated labels, yet each is associated with a different copy of a bitmap and a HREF. For example, the ticks 491 may represent weeks within a month. Because each tick 491 has its own bitmap, the user can click on one to move the pointer 492 to a particular week.

Finally, in a further embodiment of the present invention, an individual bitmap may itself be sectioned, each section being mapped to a different indicator or URL, or no URL at all. For example, the file tab HTML code above uses HTML tags <USEMAP>, <MAP> and <AREA> to specify two different URLs corresponding to the left tab and right tab within the tab_off_r bitmap. That part of the bitmap not corresponding to any tab is not mapped to an URL.

Protocol-version Dependent Forms

For various reasons, it is common during a trial for the protocol to undergo changes. Related forms must be changed to fit the new protocol when this happens. However, data entered before the change, i.e. in the old protocol, must be presented in a form corresponding to the old protocol under which it was entered.

In addition, as stated earlier, a protocol change may need to be reviewed by an Institutional Review Board at each site before it can be implemented. This can result in there being two or more active protocols at the same time. Again, the data must be presented in the form corresponding to the protocol in which the data was entered.

Figure 12A:
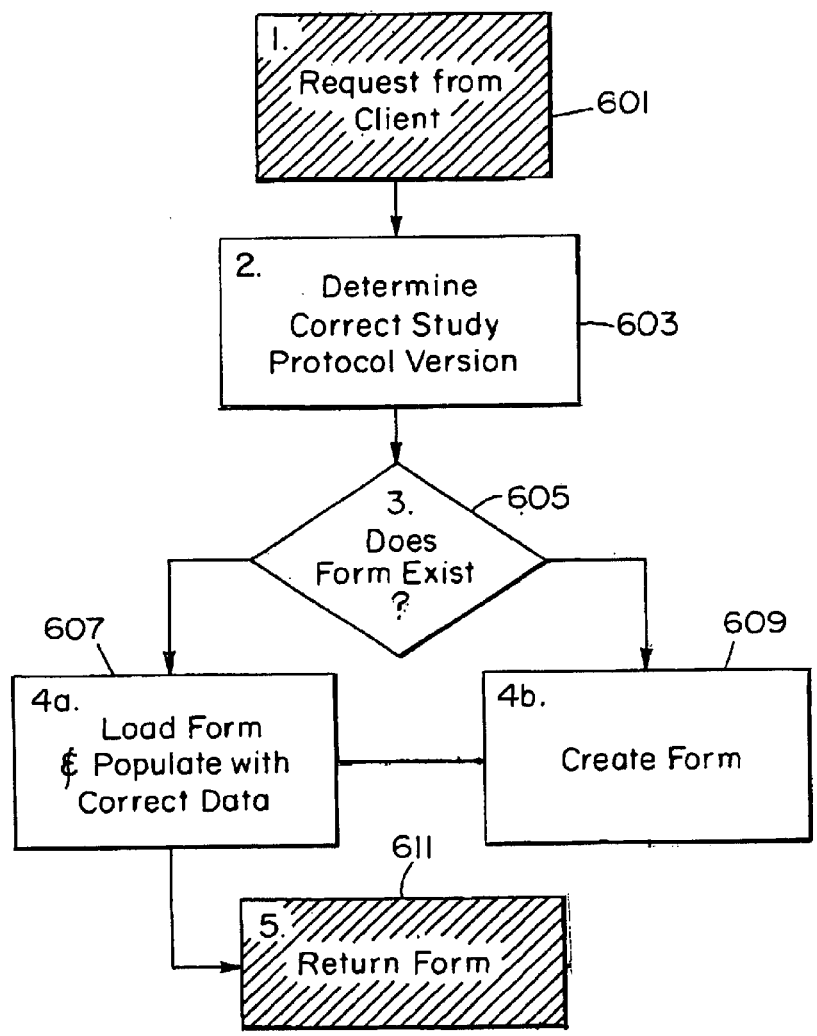
FIG. 12A is a flowchart illustrating the present invention's use of study protocol version control.

FIG. 12A is a flowchart illustrating the process at the server in deciding how to deliver a form to the browser depending on the study protocol version control. At block 601, a request is received from a client. The server determines what the correct study protocol version should be for the request based on date and time by looking up the protocol version of the CRF when data was first entered in the CRF. At block 605, the server determines whether the necessary form (CRF) already exists. If so the form is loaded and populated with the correct data (block 607). Otherwise, the form is created (block 609). Finally, in block 611, the correct populated form is returned to the requesting client.

Figure 12B:
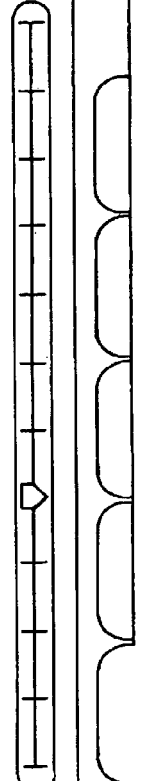
FIGS. 12B and 12C are illustrations showing the same form under two different protocol versions.
Figure 12C:
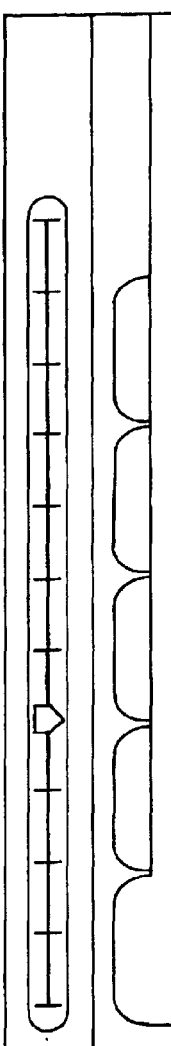

FIGS. 12B and 12C illustrate a CRF as it might appear in a first protocol (ref. 620 in FIG. 12B) and as it might appear in a second protocol (ref. 622 in FIG. 12C). In FIG. 12B, the CRF 620 has three items 621, 623, 625. Perhaps at the beginning of the trial, it was established that blood pressure would be measured twice and entered into items 623 and 625.

At some point during the trial, it is decided to change the protocol so that blood pressure is to be measured three times. The CRF would then appear as in ref. 622 in FIG. 12C, having an additional item 627 corresponding to the new third measurement.

Of course, for visits occurring prior to the protocol version change, there would only be two blood pressure measurements on file, and so the CRF as portrayed in FIG. 12B (ref. 620) is retrieved and displayed when a user examines those visits.

Integrated Help

In prior art applications, help is often available in the form of a help button, or a help link. Typically, the user clicks on the help button or link, and a general help page, often accompanied with a table of contents and/or a topic index, is retrieved from the server and displayed, replacing the original page. To find help, the user must search through the table of contents or the index, sometimes through several layers. To return to the original page, the user must either go back by clicking on a "Back" button in the browser, or optionally by clicking on a "Back to Document"—type link or button that is typically available on the help page. Several steps are thus required to obtain help about a specific topic and then return to the original page for which help was needed.

Figures 13A, 13B:
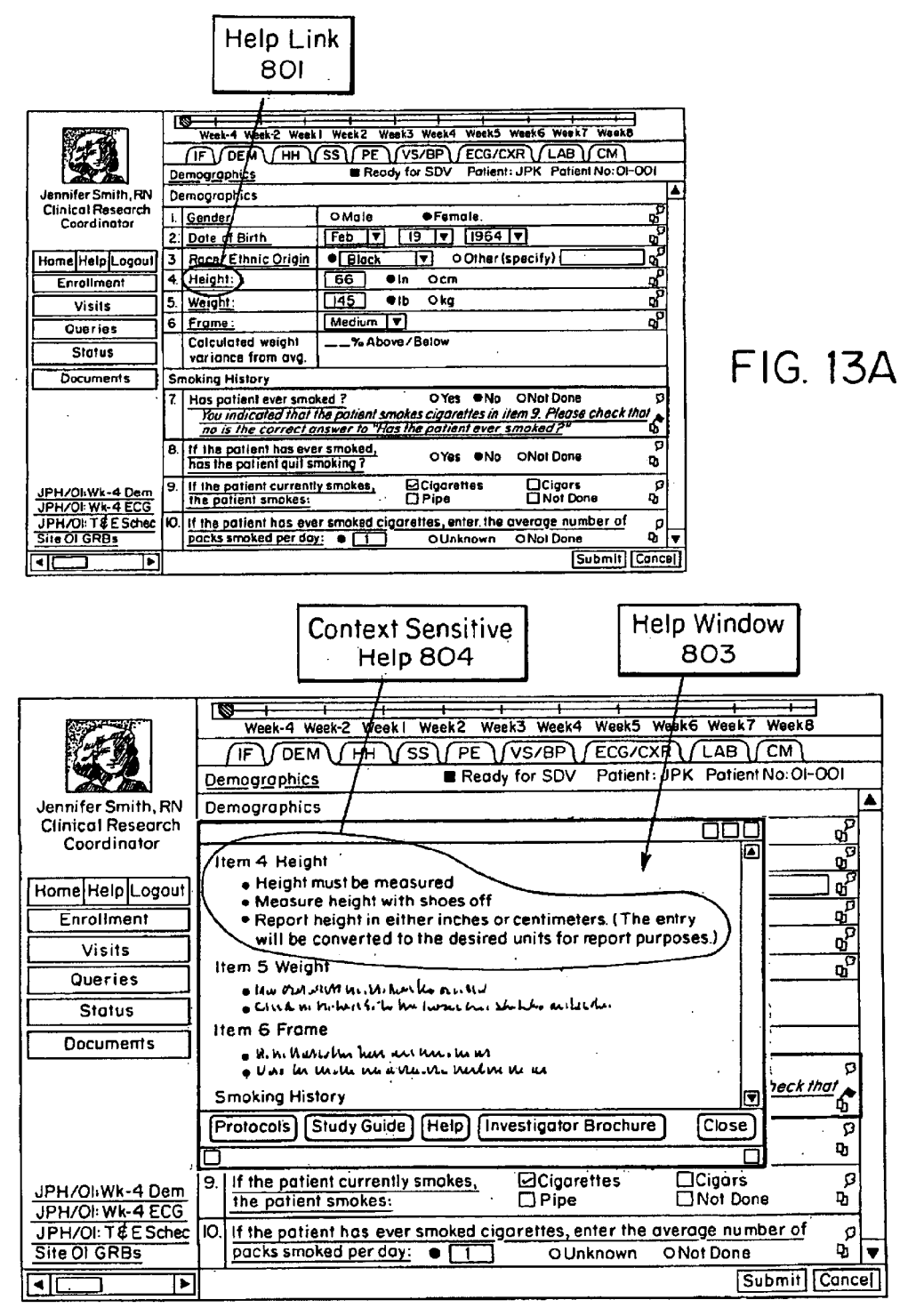
Figure 13C:
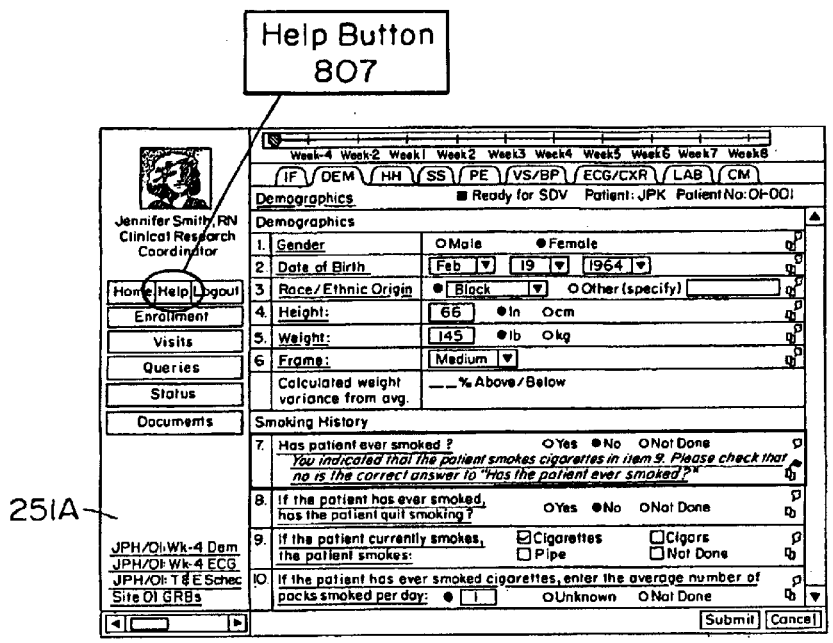
Figure 13D:
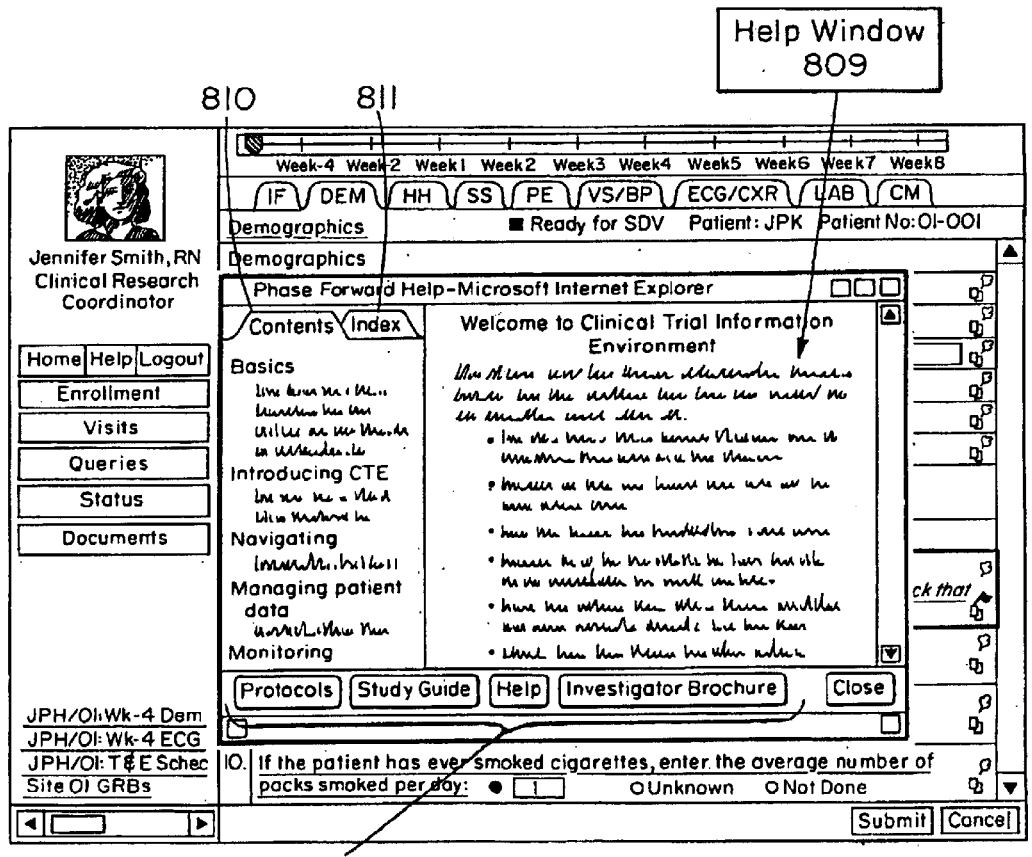

An innovative aspect of the present invention is the use of context sensitive help in a Web document. As seen in FIG. 13A, the text of each question comprises a link to one of several trial-related documents. For instance, the text 801 "Height" for item 4 is such a link. When the user clicks on the text 801, a separate help window 803 pops open, as in FIG. 13B, and context sensitive help 804 is transferred from the server and displayed in the help window 803. This context sensitive help 804 has information specific to the text 801 clicked on—here there are specific instructions as to how to measure height, e.g. shoes off. Thus the user does not have to look for the subject in an index or table of contents, and the original page is still available—the user can close the help window at any time and the original page has not been affected.

Preferably, help comes from one of three standard sources defining the clinical trial: a protocol document, an investigative brochure, or a study guide. Note that the help window 803 comprises additional button controls 805 which enable the user to go directly to related information in any of the three documents.

Figure 13E:
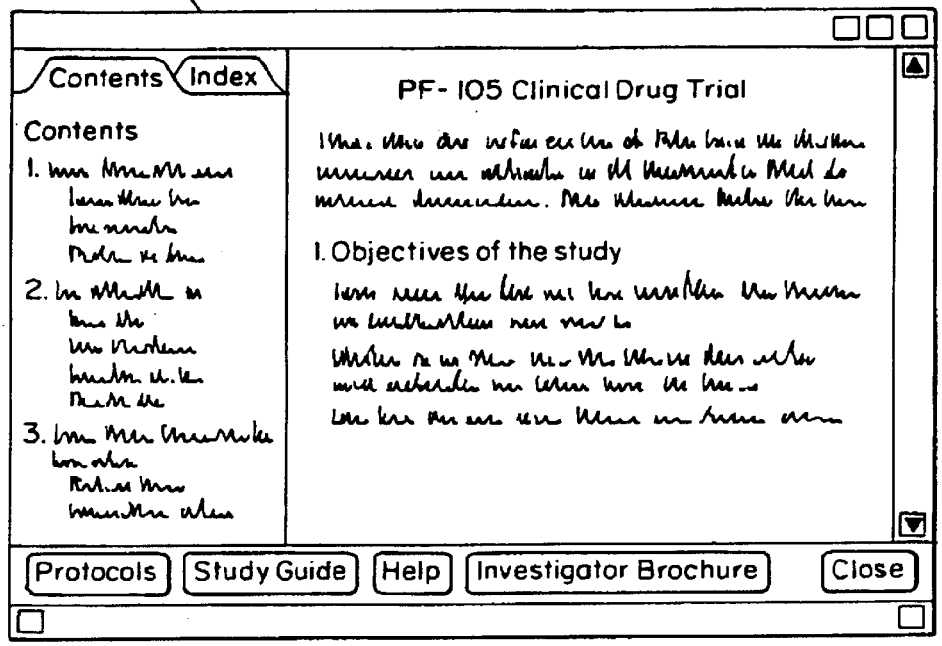
Figure 13F:
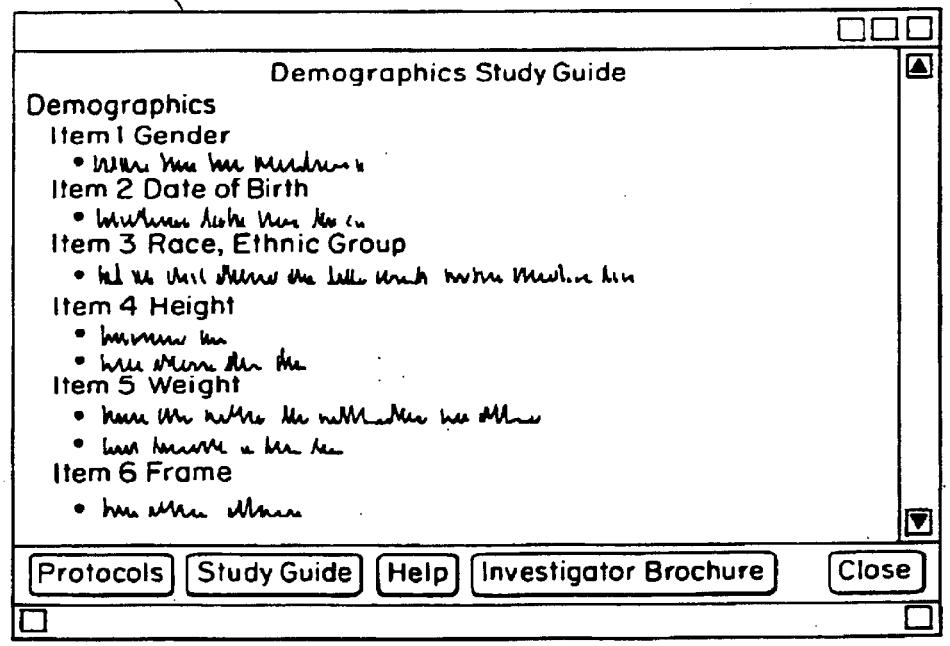

In addition, a help button 807 is always available in the main panel 251A. Clicking on this button 807 brings up a general help window 809, from which a user can browse through a table of contents 810 or an index 811 for the clinical trial documents. Again, additional buttons 805 allow the user to choose a specific document. FIGS. 13E and 13F show sample help screens for the protocol document 811 and study guide 812 respectively.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of constructing a graphical user interface (GUI) form, comprising the steps of:

creating a protocol database which is specific to an application for which data is input and displayed through a client browser, and a data database which is specific to a subject processed by the application;

dynamically generating a form document by automatically selecting and assembling template fragments from a library of template fragments according to structural information stored in the protocol database and a client context, the structural information defining hierarchies of document objects, identifying plural selectable items within plural groups of items in the form, associated with template fragments;

populating the generated form document with application data from the data database, said data associated with the selected template fragments; and publishing the populated template via a content server to the client browser as an SGML-derived form for input and display of data for the application.

2. The method of claim 1, the populated document comprising plural instances of at least one bitmap, each said bitmap instance being combined with at least one other bitmap instance to construct least one control element, the method further comprising:

receiving the data entry form from the client, clinical trial data having been entered into the form at the client; and storing, at the server, the received clinical trial data.

3. The method of claim 2, further comprising:

displaying, at a client, selected clinical trial data based on at least one of: a user, a patient, a protocol version within a clinical trial, and data previously entered.

4. The method of claim 2 wherein selected bitmaps are combined to construct a control element by placing indicators to the selected bitmaps in certain locations within the form, the browser correctly displaying the control element based on the indicators and their locations within the form.

5. The method of claim 4, the selected bitmaps including at least one instance of the least one bitmap.

6. The method of claim 2 further comprising the steps of:

partitioning a portion of the form into multiple bitmaps;

associating each different bitmap with a different indicator; and associating different instances of a single bitmap with a common indicator.

7. The method of claim 2 wherein the form includes a tab control, a single tab of the tab control comprising a first-side bitmap, a second-side bitmap, and a center bitmap.

8. The method of claim 7 wherein a single bitmap is shared between two adjacent tabs, the shared bitmap serving as the first-side bitmap for a first of the adjacent tabs and as the second-side bitmap for a second of the adjacent tabs.

9. The method of claim 2 wherein the form includes a linear control, the linear control comprising:
   button control elements spaced at intervals along a line, wherein each button control element is a bitmap or combination of bitmaps; and
   a pointer bit map to indicate a current value along the line.

10. The method of claim 2 wherein the SGML-derived form is defined with HTML.

11. The method of claim 2 wherein the SGML-derived form is defined with XML.

12. The method of claim 2 wherein the server is stateless with respect to the form's control elements.

13. The method of claim 2 wherein the indicators are uniform resource locators (URLs).

14. The method of claim 2 wherein the certain locations are table entries.

15. The method of claim 1 wherein generating the form document is further based on the data database.

16. The method of claim 1 wherein the protocol database is based on a clinical protocol.

17. The method of claim 1 wherein the template comprises a plurality of frames including control frames comprising one or more control elements, and an intermediate frame presenting a visual attribute shared by control frames to which it is adjacent, appearance of the intermediate frame depending on visual states of the adjacent control frames.

18. The method of claim 1, wherein generating the form document further comprises:
   creating a plurality of bitmaps which selectively and in combination may be constricted to present a GUI control element in any of plural states;
   specifying the form document as a Standard Generalized Markup Language (SGML)-derived document;
   and placing the bitmaps within the form document such that upon receipt of the document at the browser, the browser will display a desired GUI control.

19. The method of claim 1, further comprising
   changing a first protocol version to a second protocol version; and wherein
   generating a form document is further based on a protocol version which was active at time of entering data to be displayed.

20. The method of claim 1 wherein rules associated with the displayed for are based on the protocol version which was active at the time of entering data to be displayed in the form.

21. The method of claim 1, further comprising:
   discouraging inadvertent use by
      requiting an authentication procedure for each user, and displaying a picture of an authenticated user.

22. The method of claim 1, wherein the populated form document has at least one question to which a user must respond to provide clinical data, further comprising:
   creating links between text of each question and detailed information related to the question; and
   if the user clicks on text of the question, displaying detailed information corresponding to the question.

23. The method of claim 22 wherein the detailed information displayed is a help document defining the clinical trial.

24. The method of claim 23 wherein the help document is one of a protocol document, an investigative brochure, and a study guide.

25. The method of claim 23 wherein the help document comprises all of a protocol document, an investigative brochure, and a study guide.

26. The method of claim 25 wherein the user can walk through each of the protocol document, investigative brochure and study guide.

27. The method of claim 26 wherein the detailed information displayed is from a section of the protocol document investigative brochure, or study guide, which section pertains immediately to the question to which the user must respond.

28. The method of claim 1, wherein the application is a clinical trial application, the method further comprising the steps of:
   providing a user login procedure;
   upon a user logging in presenting to the user a dashboard screen comprising information regarding the trial, the dashboard screen being customized for the user.

29. The method of claim 28 wherein the information comprises trial-related news.

30. The method of claim 28 wherein the information comprises alerts.

31. The method of claim 28 wherein the information comprises statistical information.

32. The method of claim 28 wherein the information comprises progress reports.

33. The method of claim 28 wherein the information comprises a list of work to be completed.

34. The method of claim 1 wherein the application is a clinical trial.

35. The method of claim 1, at least one template fragment including a script which implements at least one rule.

36. The method of claim 35, the at least one rule checking for inconsistencies in data entered into the form.

37. A system for constructing a graphical user interface (GUI) form, comprising:
   a protocol database which is specific to an application for which data is input and displayed through a client browser;
   a data database which is specific to a subject processed by the application;
   a generator which dynamically generates a form document by automatically selecting and assembling template fragments from a library of template fragments according to structural information stored in the protocol database and a client context, the structural information defining hierarchies of document objects, identifying plural selectable items within plural groups of items in the form, associated with template fragments;
   a populator which populates the generated form document with application data from the data database, said data associated with the selected template fragments; and
   a content server which publishes the populated template to the client browser as an SGML-derived form for input and display of data for the application.

38. The system of claim 37, the populated document comprising plural instances of at least one bitmap, each said bitmap instance being combined with at least one other bitmap instance to construct at least one control element, the system further comprising:
   means for receiving the data entry form from the client, clinical trial data having been entered into the form at the client; and
   a server for storing the received clinical trial data.

39. The system of claim 38 wherein selected bitmaps are combined to construct a control element is specified by placement of indicators to the selected bitmaps in certain locations within the form, the browser correctly displaying the control element based con the indicators and their locations within the form.

40. The system of claim 39 wherein the indicators are uniform resource locators (URLs).

41. The system of claim 39 wherein the certain locations are table entries.

42. The system of claim 38 wherein the form comprises multiple bitmaps, each different bitmap being associated with a different indicator, and different instances of a single bitmap bring associated with a common indicator.

43. The system of claim 38 wherein the SGML-derived form is defined with HTML.

44. The system of claim 38 wherein the server is stateless with respect to the form's control elements.

45. The system of claim 38, wherein selected clinical trial data are displayed at a client, the selection being based on at least one of: a user, a patient, a protocol version within a clinical trial, and data previously entered.

46. The system of claim 38, further comprising:
   an authentication procedure for each user; and
   a picture display, within the form, of an authenticated user.

47. The system of claim 38, wherein the form has at least one question to which a user must respond to provide clinical data; and
   links between text of each question and detailed information related to the question, the detailed information existing in at least one on-line document, such that if the user clicks on text of the question, displaying detailed information corresponding to the question is displayed.

48. The system of claim 37, the template comprising:
   an intermediate frame which presents a visual attribute shared by control frames to which it is adjacent, appearance of the intermediate frame depending on visual states of the adjacent control frames.

49. A system for constructing a graphical user interface (GUI) form, comprising:
   protocol database means specific to an application for which data is input and displayed through a client browser, and data database means which is specific to a subject processed by the application;
   generation means for dynamically generating a form document by automatically selecting and assembling template fragments from a library of template fragments according to structural information stored in the protocol database means and a client context, the structural information defining hierarchies of document objects, identifying plural selectable items within plural groups of items in the form, associated with template fragments;
   populating means for populating the generated form document with application data from the data database means, said data associated with the selected template fragments; and
   publishing means for publishing the populated template via a content server to the client browser as an SGML-derived form for input and display of data for the application.

* * * * *

UNITED STATES PATENT AND TRADEMARK OFFICE
CERTIFICATE OF CORRECTION

PATENT NO. : 6,820,235 B1
DATED : November 16, 2004
INVENTOR(S) : Paul A. Bleicher et al.

It is certified that error appears in the above-identified patent and that said Letters Patent is hereby corrected as shown below:

Column 33,
Lines 17 and 19, delete "2" and insert -- 4 --;
Line 34, delete "constricted" and insert -- constructed --;
Line 48, delete "for" and insert -- form --.

Column 34,
Line 8, after "document" insert -- , --;
Line 16, after "in", insert -- , --.

Column 35,
Line 3, delete "con" and insert -- on --;
Line 12, delete "bring" and insert -- being --.

Signed and Sealed this

Eleventh Day of January, 2005

JON W. DUDAS
*Director of the United States Patent and Trademark Office*